(12) United States Patent
Lemelin et al.

(10) Patent No.: US 9,482,650 B2
(45) Date of Patent: Nov. 1, 2016

(54) STATIC AND DYNAMIC SEALS

(75) Inventors: Marc E. Lemelin, Douglas, MA (US);
Tony A. Lin, Ashland, MA (US); Mark W. Moeller, Kingston, MA (US);
Stanislaw Koziol, Wrentham, MA (US);
James E. Usowicz, Webster, MA (US)

(73) Assignee: Waters Technologies Corporation, Milford, MA (US)

( * ) Notice: Subject to any disclaimer, the term of this patent is extended or adjusted under 35 U.S.C. 154(b) by 857 days.

(21) Appl. No.: 13/520,462

(22) PCT Filed: Jan. 11, 2011

(86) PCT No.: PCT/US2011/020745
§ 371 (c)(1),
(2), (4) Date: Nov. 16, 2012

(87) PCT Pub. No.: WO2011/085341
PCT Pub. Date: Jul. 14, 2011

(65) Prior Publication Data
US 2013/0049302 A1    Feb. 28, 2013

Related U.S. Application Data

(60) Provisional application No. 61/293,879, filed on Jan. 11, 2010.

(51) Int. Cl.
*F16J 15/02* (2006.01)
*G01N 30/60* (2006.01)
*F16J 15/10* (2006.01)
*G01N 30/20* (2006.01)

(52) U.S. Cl.
CPC ......... *G01N 30/6026* (2013.01); *F16J 15/102* (2013.01); *G01N 30/20* (2013.01); *G01N 2030/202* (2013.01); *Y10T 29/49* (2015.01)

(58) Field of Classification Search
CPC ............ F16J 15/02; F16J 15/06; F16J 15/10; F16J 15/102
See application file for complete search history.

(56) References Cited

U.S. PATENT DOCUMENTS

| | | | |
|---|---|---|---|
| 4,084,440 A | 4/1978 | Carpenter et al. | |
| 4,300,393 A | 11/1981 | Stearns | |
| 2001/0035516 A1 | 11/2001 | Nichols et al. | |
| 2003/0143123 A1 | 7/2003 | Maeda | |
| 2007/0095158 A1 | 5/2007 | Maeda | |
| 2007/0157709 A1 | 7/2007 | Gamble et al. | |
| 2009/0028988 A1* | 1/2009 | Gunther | 425/564 |
| 2009/0050212 A1 | 2/2009 | Dourdeville et al. | |
| 2011/0247405 A1* | 10/2011 | Yasunaga et al. | 73/61.55 |

OTHER PUBLICATIONS

Japanese Office Action dated Jul. 15, 2014 for Japanese Application No. 2012-548219.

(Continued)

*Primary Examiner* — Gilbert Lee
(74) *Attorney, Agent, or Firm* — Muirhead and Saturnelli, LLC

(57) ABSTRACT

Described are techniques for use with a sealing member forming a static seal or a dynamic seal at a surface thereof. The sealing member has at least the surface thereof formed from one of VESPEL® SCP 5000 material or VESPEL® SCP 50094 material.

9 Claims, 38 Drawing Sheets

(56) References Cited

OTHER PUBLICATIONS

Lough, W. John, et al.,"Analyte adsorption in liquid chromatography valve injectors for samples in non-eluting solvents," Journal of Chromatography A, vol. 726, No. 1, Mar. 1, 1996, pp. 65-75, XP004039485, ISSN: 0021-9673, DOI: 10.1016/0021-9673(95)01070-X.

"New polyimide offers higher temperatures," Sealing Technology, vol. 2009, No. 4, Apr. 1, 2009, pp. 2, XP026043965, ISSN: 1350-4789, DOI: 10.1016/S13504789(09)70164-3.

European Search Report dated Apr. 4, 2014 for EP11732294.1.

Japanese Office Action dated Mar. 3, 2015 for Japanese Application No. 2012-548219.

* cited by examiner

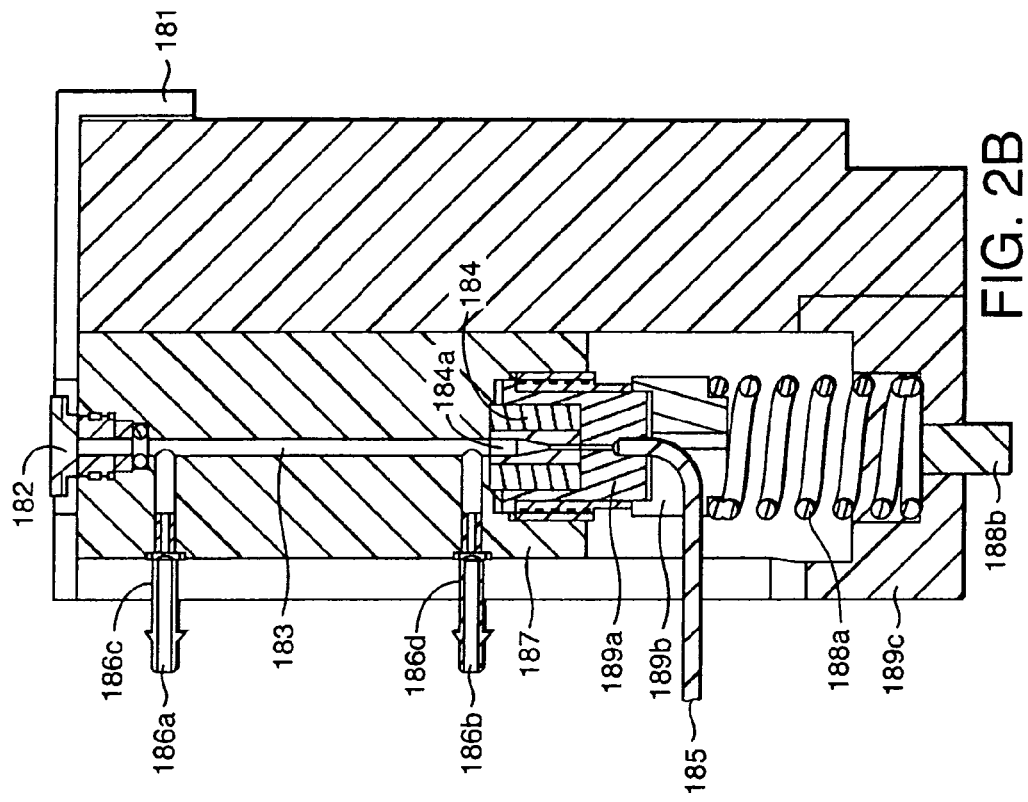
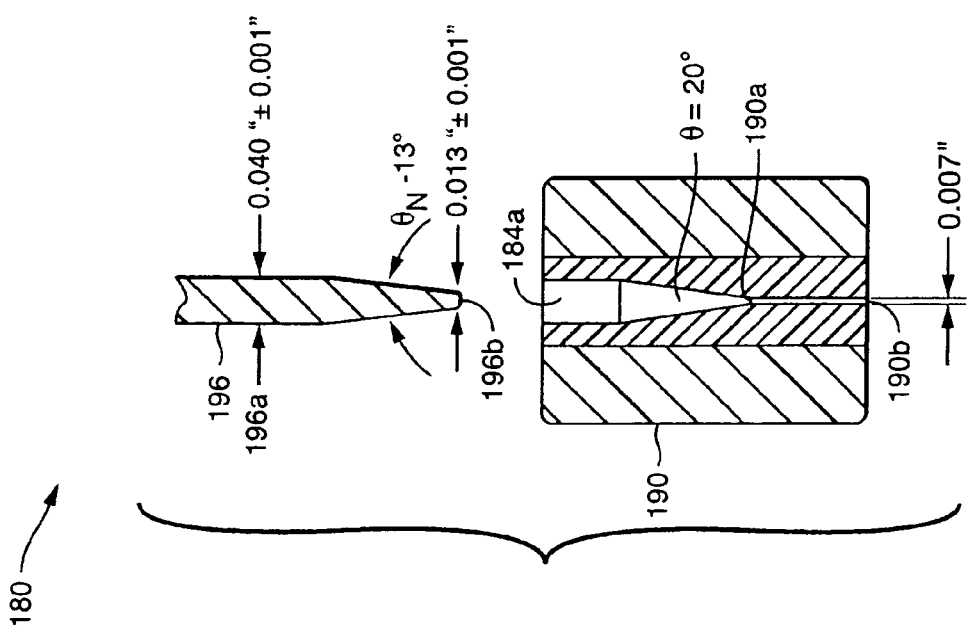
FIG. 2B
FIG. 2A

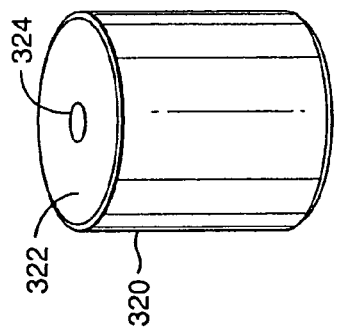
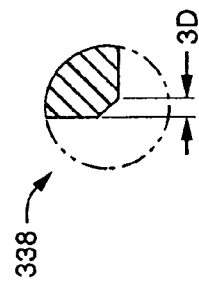
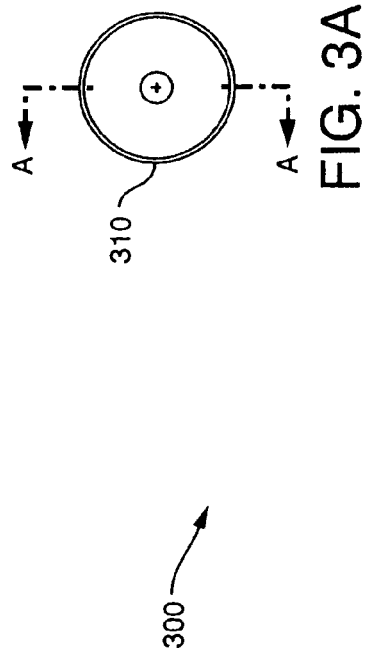
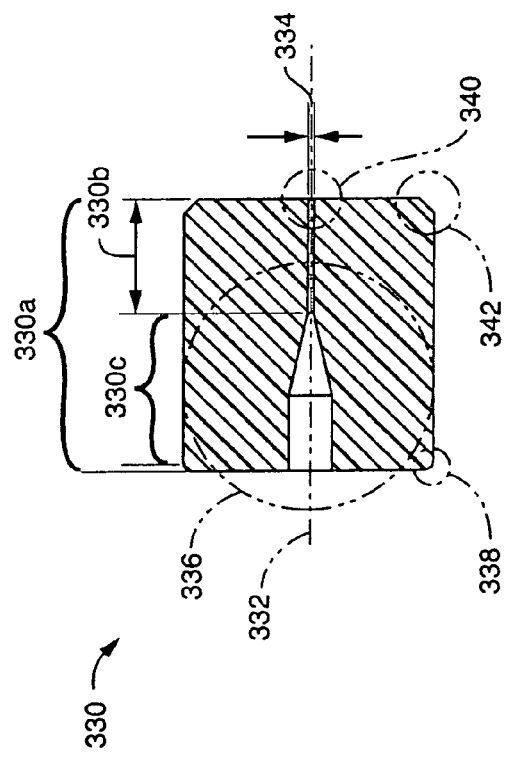

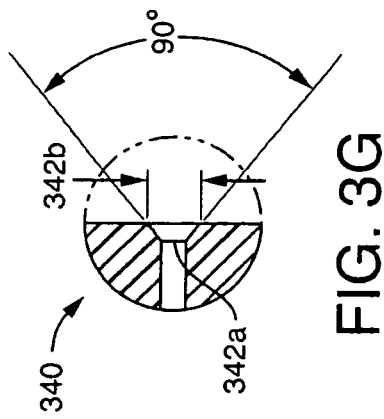
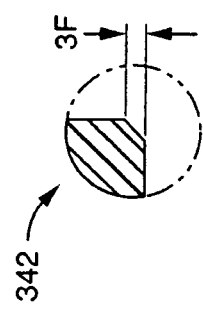
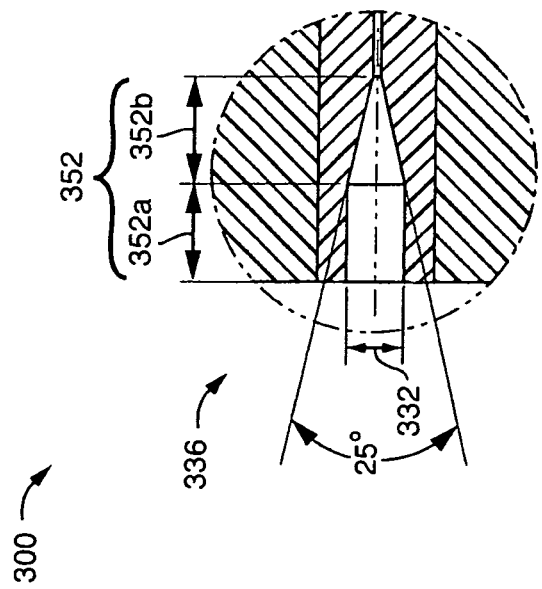
FIG. 3G
FIG. 3F
FIG. 3E

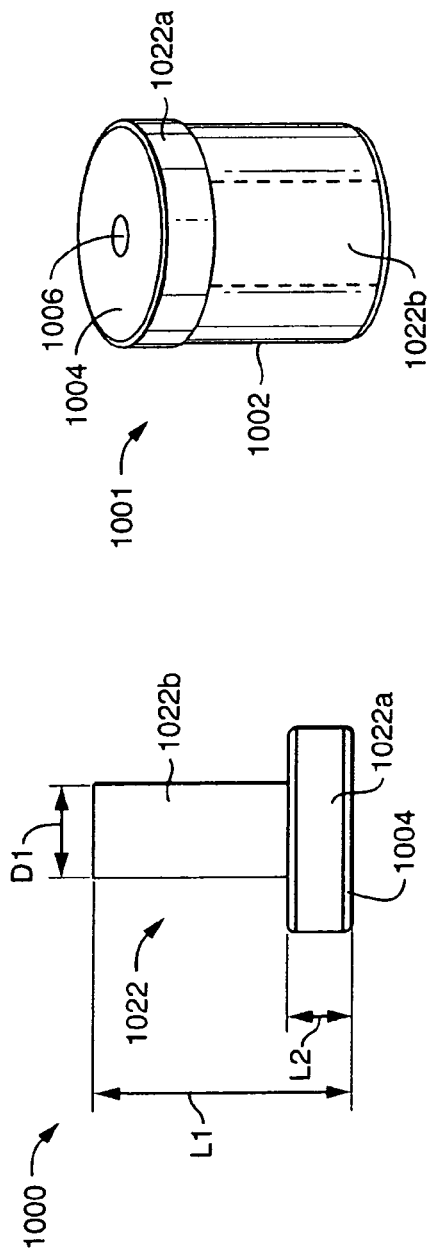
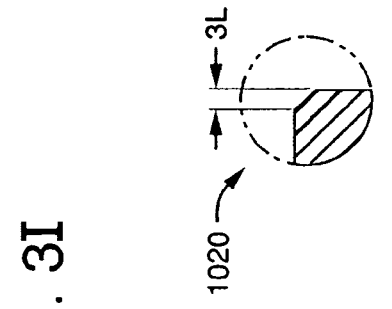
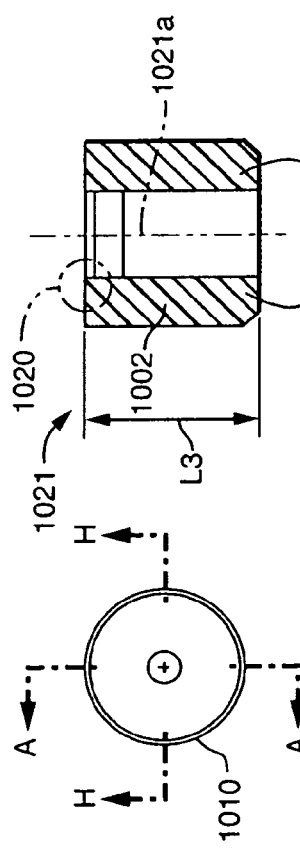
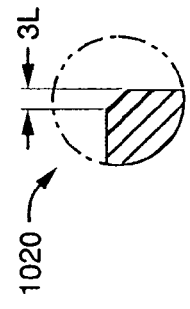

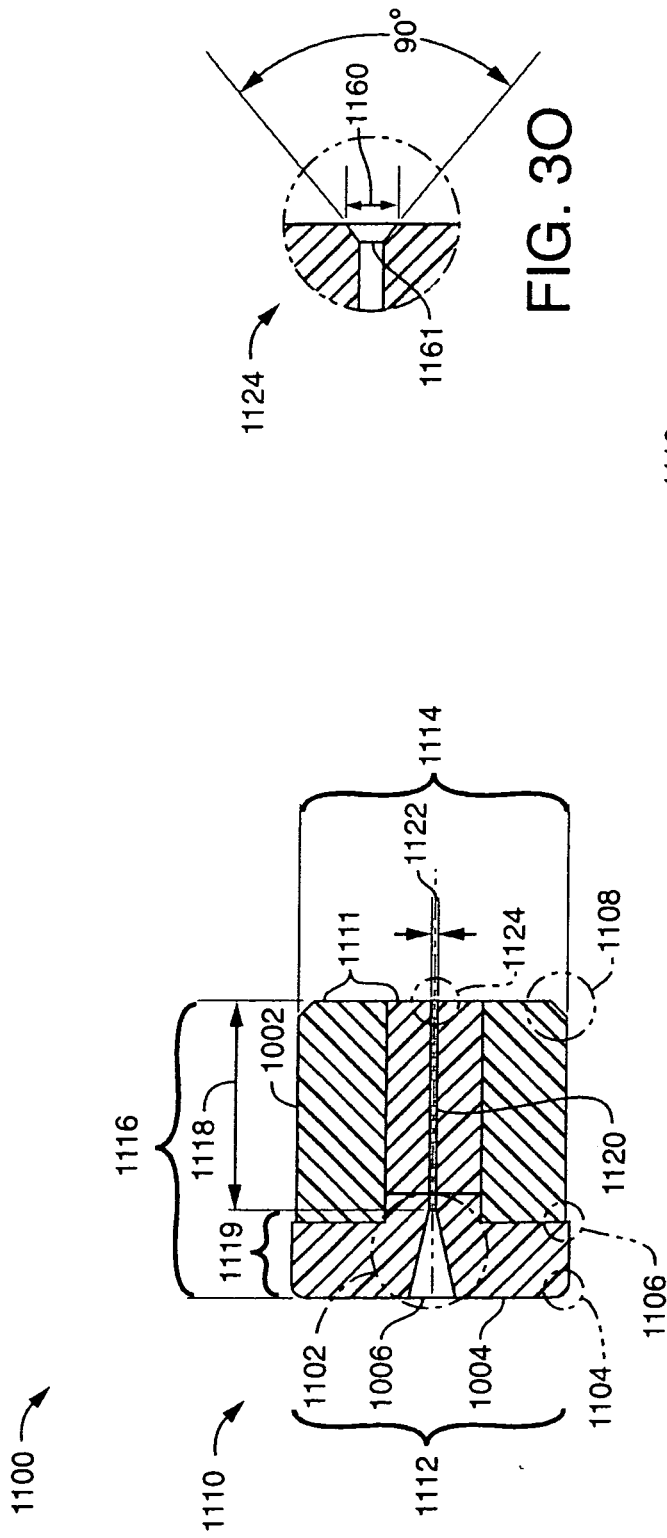

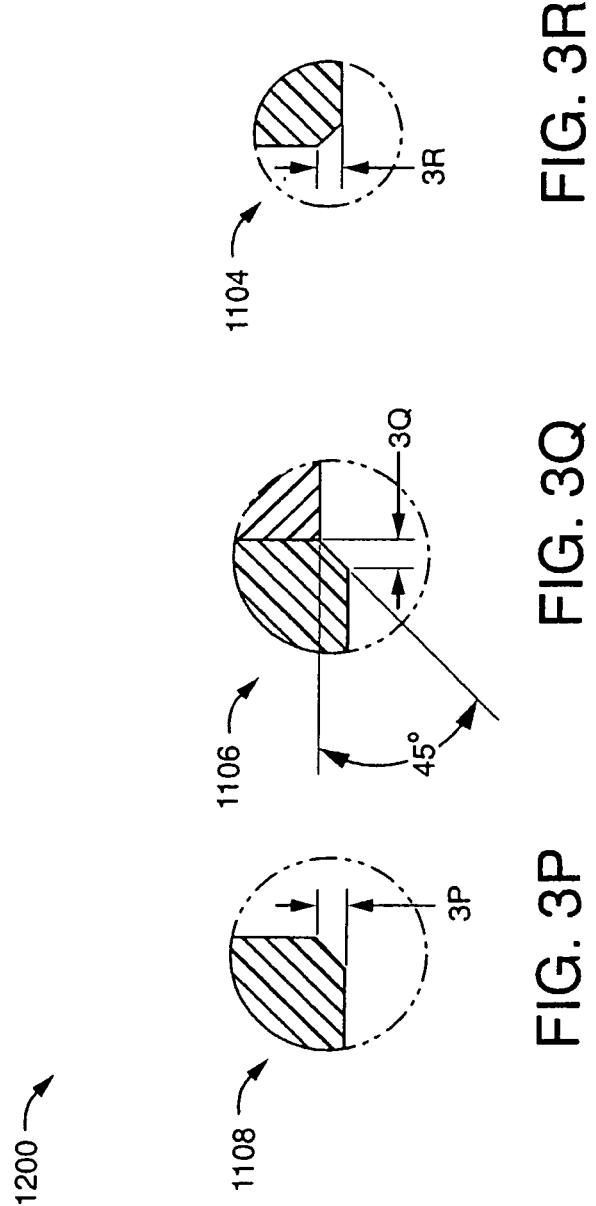

| SPC 5000 | | | | |
|---|---|---|---|---|
| TYPICAL ISO PROPERTIES | | | | |
| DuPont™ Vespel® SCP-5000 IS A NEW UNFILLED POLYIMIDE POLYMER THAT OFFERS HIGH MODULUS AND SURFACE HARDNESS AND IMPROVED DIMENSIONAL STABILITY. COMPARED TO TRADITIONAL POLYIMIDES, IT OFFERS BETTER STRENGTH AND STIFFNESS AT HIGH TEMPERATURES. | | | | |
| MECHANICAL PROPERTY | TEMPERATURE | ASTM METHOD | SI (ENGLISH) UNITS | TYPICAL VALUES |
| TENSILE STRENGTH | 23°C (73°F) 260°C (500°F) | D-638 D-1708 SPECIMEN | MPa (kpsi) | 163 (23.6) 62 (9.0) |
| TENSILE ELONGATION | 23°C (73°F) 260°C (500°F) | D-638 D-1708 SPECIMEN | % | 7.5 49 |
| YOUNG'S MODULUS | 23°C (73°F) 260°C (500°F) | D-638 D-1708 SPECIMEN | MPa (kpsi) | 3,990 (580) 2,370 (340) |
| FLEXURAL STRENGTH | 23°C (73°F) 260°C (500°F) | D-790 | MPa (kpsi) | 254 (36.8) 96.5 (14.0) |
| FLEXURAL MODULUS | 23°C (73°F) 260°C (500°F) | D-790 | MPa (kpsi) | 5,760 (836) 3,007 (436) |
| COMPRESSIVE STRENGTH | 23°C (73°F) 260°C (500°F) | D-695 | MPa (kpsi) | 640 (92.9) 549 (79.6) |
| COMPRESSIVE MODULUS | 23°C (73°F) 260°C (500°F) | D-695 | MPa (kpsi) | 9,060 (1,314) 3,698 (536) |
| COMPRESSIVE STRESS AT 10% STRAIN | 23°C (73°F) 260°C (500°F) | D-695 | MPa (kpsi) | 230 (33.4) 73.6 (10.7) |
| DEFORMATION UNDER LOAD 24 HOURS, 14 MPa (2kpsi) | 23°C (73°F) | D-621 | % DEFORMATION | 0.05 |
| ROCKWELL "E" HARDNESS | — | D-785 | — | 95 |

| PROPERTY | TEMPERATURE | ASTM METHOD | SI (ENGLISH) UNITS | TYPICAL VALUES |
|---|---|---|---|---|
| THERMAL PROPERTY | TEMPERATURE | ASTM METHOD | SI (ENGLISH) UNITS | TYPICAL VALUES |
| COEFFICIENT OF THERMAL EXPANSION | 23°C - 300°C (73°F - 572°F) | E-831 | m/m °C or m/m K (in/in°F) | 45 X 10⁻⁶ (26 X 10⁻⁶) |
| SPECIFIC HEAT | 60°C (140°F) | E-1269 | J/kg °C (Btu/lb °F) | 9.2 X 10⁵ (0.22) |
| ELECTRICAL PROPERTY | TEMPERATURE | ASTM METHOD | SI (ENGLISH) UNITS | TYPICAL VALUES |
| DIELECTRIC CONSTANT, 10⁴ Hz / 10⁶ Hz | 23°C (73°F) | D-150 | — | 3.3 / 3.3 |
| DIELECTRIC FACTOR, 10⁴ Hz / 10⁶ Hz | 23°C (73°F) | D-150 | — | 0.001 / 0.001 |
| VOLUME RESISTIVITY | 23°C (73°F) | D-257 | Ohm-m | 10¹⁴ |
| SURFACE RESISTIVITY | 23°C (73°F) | D-257 | Ohm-m | 10¹⁵ |
| WEAR PROPERTY | TEMPERATURE | ASTM METHOD | SI (ENGLISH) UNITS | TYPICAL VALUES |
| COEFFICIENT OF FRICTION, UNLUBRICATED, AIR • 0.88/25K) PV • 3.50 (100K) PV | 0.7 m/s (134 fpm) 2.0 m/s (400 fpm) | 1.3 MPa (187 psi) 1.7 MPa (250 psi) | FALEX | 0.26 / 0.15 |
| OTHER PROPERTY | TEMPERATURE | ASTM METHOD | SI (ENGLISH) UNITS | TYPICAL VALUES |
| SPECIFIC GRAVITY | — | D-792 | — | 1.46 |
| WATER ABSORPTION AFTER 24 HOURS | 23°C (73°F) | D-570 | % WEIGHT CHANGE | 0.08 |

FIG. 5B

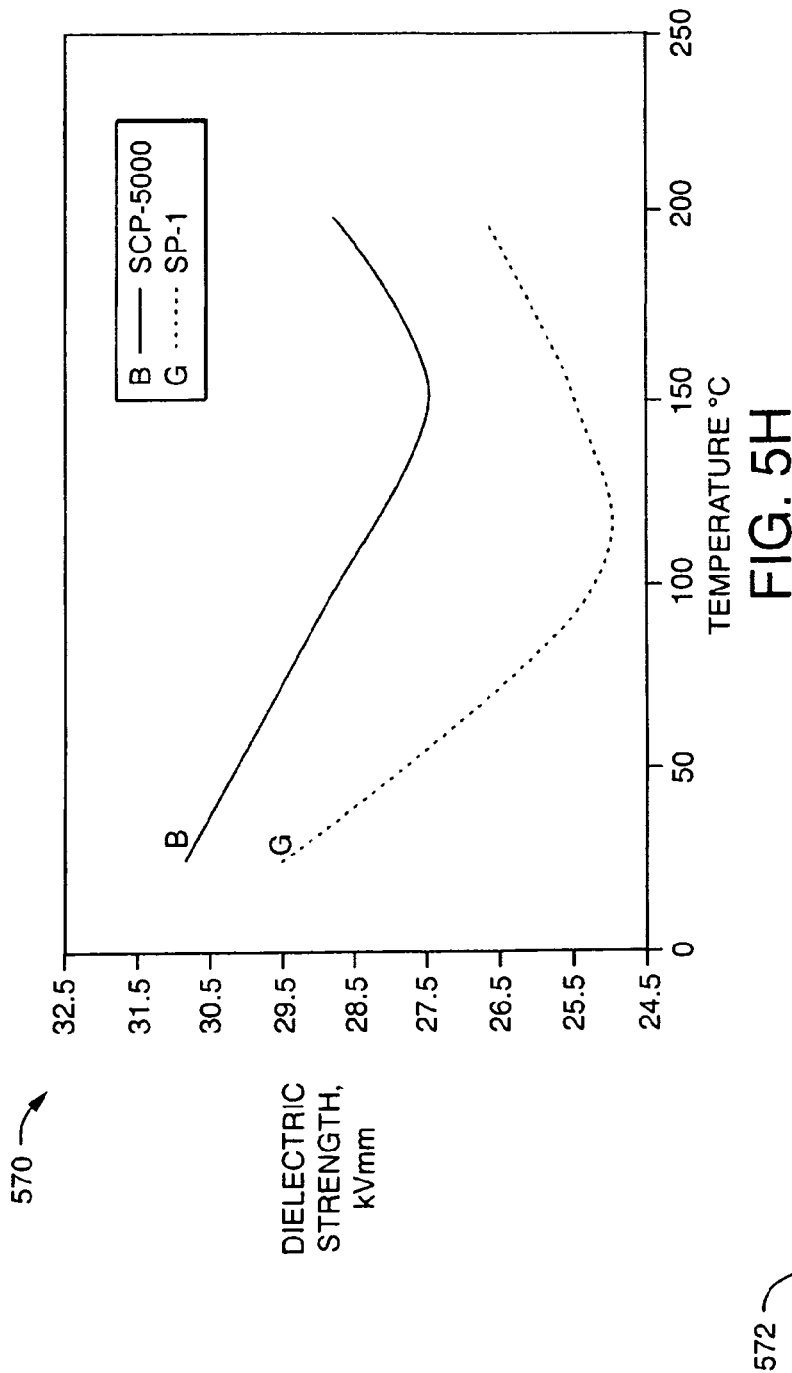

TYPICAL PROPERTIES OF VESPEL SCP-5000 ISO — 620

| MECHANICAL | | TEST METHOD | SI UNITS | ENGLISH UNITS |
|---|---|---|---|---|
| TENSILE STRENGTH | 23°C/73F°<br>260°C/500°F | ASTM D-1708 | 160 MPa<br>62 MPa | 23.4 kpsi<br>8.9 kpsi |
| ELONGATION AT BREAK | 23°C/73F°<br>260°C/500°F | ASTM D-1708 | 70%<br>>20% | 70%<br>>20% |
| COMPRESSIVE STRESS AT 1% | 23°C/73F°<br>260°C/500°F | ASTM D-695 | 60 MPa<br>32 MPa | 8.7 kpsi<br>4.7 kpsi |
| COMPRESSIVE STRESS AT 10% | 23°C/73F°<br>260°C/500°F | ASTM D-695 | 230 MPa<br>74 MPa | 33 kpsi<br>11 kpsi |
| COMPRESSIVE MODULUS | 23°C/73F°<br>260°C/500°F | ASTM D-695 | 9,200 MPa<br>3,700 MPa | 1,300 kpsi<br>540 kpsi |
| FLEXURAL STRENGTH | 23°C/73F°<br>260°C/500°F | ASTM D-790 | 247 MPa<br>97 MPa | 38 kpsi<br>14 kpsi |
| FLEXURAL MODULUS | 260°C/500F°<br>23°C/73°F | ASTM D-790 | 5,700 MPa<br>3,000 MPa | 840 kpsi<br>440 kpsi |
| SURFACE HARDNESS | 23°C/73°F | ASTM D-785 ROCKWELL E | 94 - 95 | 94 - 95 |
| THERMAL | | TEST MATERIAL | SI UNITS | ENGLISH UNITS |
| COEFFICIENT OF LINEAR THERMAL EXPANSION | | | | |
| PARALLEL | 23-300°C/<br>73-572°F | ASTM D-696 | 44 m$^{-6}$/m°C | 24.0 in$^{-6}$/in°F |
| PERP. | 23-300°C/<br>73-572°F | ASTM D-696 | 47 m$^{-6}$/m°C | 26.0 in$^{-6}$/in°F |

FIG. 6F

| ELECTRIC | | TEST METHOD | SI UNITS | ENGLISH UNITS |
|---|---|---|---|---|
| DIELECTRIC CONSTANT AT $10^4$ Hz | 23°C/73F° | ASTM D-150 | 3.3 | 3.3 |
| DIELECTRIC CONSTANT AT $10^6$ Hz | 23°C/73F° | ASTM D-150 | 3.3 | 3.3 |
| DISSIPATION FACTOR AT $10^4$ Hz | 23°C/73F° | ASTM D-150 | 0.001 | 0.001 |
| DISSIPATION FACTOR AT $10^6$ Hz | 23°C/73F° | ASTM D-150 | 0.001 | 0.001 |
| VOLUME RESISTIVITY | 23°C/73F° | ASTM D-257 | $10^{14}$ Ohm-m | $10^{14}$ Ohm-m |
| SURFACE RESISTIVITY | 23°C/73F° | ASTM D-257 | $10^{15}$ Ohm | $10^{15}$ Ohm |
| OTHER PROPERTIES | | TEST METHOD | SI UNITS | ENGLISH UNITS |
| SPECIFIC GRAVITY | 23°C/73F° | ASTM D-792 | 1.43 | 1.43 |
| WATER ABSORPTION AT 100%. 24 HR (WEIGHT CHANGE) | | ASTM D-570 | 0.08% | 0.08% |

FIG. 6G

| DUPONT VESPEL SCP - 50094 DIRECT FORM | | | | | |
|---|---|---|---|---|---|
| MECHANICAL PROPERTY | TEMPERATURE | PRESSURE | ASTM METHOD | SI ENGLISH UNITS | TYPICAL PROPERTIES |
| TENSILE STRENGTH | 23°C (73F°)<br>260°C (500°F) | — | D-638 METHOD/<br>E-8 SPECIMEN | MPa (kpsi) | 88 (12.8)<br>45 (6.6) |
| ELONGATION | 23°C (73F°)<br>260°C (500°F) | — | D-638 METHOD/<br>E-8 SPECIMEN | % | 2.1<br>4.6 |
| YOUNG'S MODULUS | 23°C (73F°)<br>260°C (500°F) | — | D-638 METHOD/<br>E-8 SPECIMEN | MPa (kpsi) | 6490 (941)<br>3720 (539) |
| COMPRESSIVE STRENGTH | 23°C (73F°)<br>260°C (500°F) | — | D-695 | MPa (kpsi) | 170 (24.7)<br>77 (11.2) |
| COMPRESSIVE STRAIN, ULTIMATE | 23°C (73F°)<br>260°C (500°F) | — | D-695 | % | 18<br>31 |
| COMPRESSIVE STRESS AT 10% STRAIN | 23°C (73F°)<br>260°C (500°F) | — | D-695 | MPa (kpsi) | 168 (24.4)<br>64 (9.3) |
| FLEXURAL MODULUS | 23°C (73F°)<br>260°C (500°F) | — | D-790 | MPa (kpsi) | 5170 (750)<br>2700 (392) |
| FLEXURAL STRENGTH | 23°C (73F°)<br>260°C (500°F) | — | D-790 | MPa (kpsi) | 109 (15.8)<br>69 (10.0) |
| POISSON'S RATIO | 23°C (73F°)<br>190°C (374°F) | — | D-638 | | 0.25<br>0.32 |

FIG. 7A

| ROCKWELL "E" HARDNESS | 23°C (73F°) | — | D-785 | | 70.4 |
|---|---|---|---|---|---|
| SPECIFIC GRAVITY | 23°C (73F°) | — | D-792 | | 1.44 |
| DEFORMATION UNDER LOAD, 10 MINUTES PERMANENT DEFORMATION | 23°C (73F°) | 14 MPa (2.0 kpsi) | D-621 | % | 0.03<br>0.04 |
| COMPRESSIVE CREEP 10 Hrs<br>100 Hrs<br>1000 Hrs | 23°C (73F°) | 10 MPa (1.5 kpsi) | D-2990 | % | 0.02<br>0.03<br>0.05 |
| COMPRESSIVE CREEP 10 Hrs<br>100 Hrs<br>1000 Hrs | 23°C (73F°) | 14 MPa (2.5 kpsi) | D-2990 | % | 0.04<br>0.06<br>0.09 |
| WATER ABSORPTION | 23°C (73F°) | — | D-570 | % WEIGHT CHANGE | 0.96 |

| DUPONT VESPEL SCP - 50094 DIRECT FORM ||||||
| THERMAL PROPERTY | TEMPERATURE | PRESSURE | ASTM METHOD | SI ENGLISH UNITS | TYPICAL PROPERTIES |
| --- | --- | --- | --- | --- | --- |
| COEFFICIENT OF THERMAL EXPANSION, PARALLEL PERPENDICULAR | 23-300°C (73-572°F) | — | E-831 | m/m°C (m/m°F) | $60.1 \times 10^{-6}$ ($33.4 \times 10^{-6}$) <br> $34.1 \times 10^{-6}$ ($18.9 \times 10^{-6}$) |
| THERMAL CONDUCTIVITY | 50°C (122°F) <br> 100°C (212°F) <br> 150°C (302°F) <br> 200°C (392°F) <br> 250°C (482°F) <br> 300°C (572°F) | — | F-433 | W/mK (Btu/hr IN °F) | 0.39 (0.02) <br> 0.40 (0.02) <br> 0.41 (0.02) <br> 0.41 (0.02) <br> 0.41 (0.02) <br> 0.43 (0.02) |
| SPECIFIC HEAT | 60°C (140°F) | — | DSC | J/kg.°C (Btu/lb°F) | $8.96 \times 10^{-5}$ (0.214) |
| HEAT DEFLECTION TEMP. IN TIN BISMUTH, PARALLEL PERPENDICULAR | | 1.8 MPa (0.26 kpsi) | D-648 | °C (°F) | 334 (634) <br> 336 (637) |

FIG. 7C

| ELECTRICAL PROPERTY | TEMPERATURE | PRESSURE | ASTM METHOD | SI ENGLISH UNITS | TYPICAL PROPERTIES |
|---|---|---|---|---|---|
| DIELECTRIC STRENGTH | 23°C/73F° | — | D-149 | VOLTS/mil | 413 |
| VOLUME RESISTIVITY | 23°C/73F° | — | D-257 | Ohm-cm (Ohm-in) | $2.18 \times 10^{16}$ ($8.57 \times 10^{15}$) |
| SURFACE RESISTIVITY | 23°C/73F° | — | D-257 | Ohm/sq | $1.56 \times 10^{17}$ ($6.15 \times 10^{16}$) |
| DIELECTRIC CONSTANT, $10^2$Hz $10^4$Hz $10^6$Hz | 23°C/73F° | | D-150 | | 5.5 5.4 5.4 |
| DISSIPATION FACTOR, $10^2$Hz $10^4$Hz $10^6$Hz | 23°C/73F° | | D-150 | | 0.002 0.005 0.002 |

| WEAR PROPERTY | VELOCITY | PRESSURE | ASTM METHOD | SI ENGLISH UNITS | TYPICAL PROPERTIES |
|---|---|---|---|---|---|
| COEFFICIENT OF FRICTION, UNLUBRICATED, AIR 25K PV 100K PV 300K PV | 0.7 m/s (134 fpm) 2.0 m/s (400 fpm) 3.0 m/s (585 fpm) | 1.3 MPa (187 psi) 1.7 MPa (250 psi) 3.5 MPa (500 psi) | FALEX | | 0.253 0.064 0.084 |
| WEAR FACTOR, UNLUBRICATED, AIR 25K PV 100K PV 300K PV | 0.7 m/s (134 fpm) 2.0 m/s (400 fpm) 3.0 m/s (585 fpm) | 1.3 MPa (187 psi) 1.7 MPa (250 psi) 3.5 MPa (500 psi) | FALEX | mm-sec/MPa-m-hr (in3-min/ft-lb-hr) | $1.0 \times 10^{-3}$ ($13 \times 10^{-10}$) $0.6 \times 10^{-3}$ ($8 \times 10^{-10}$) $1.2 \times 10^{-3}$ ($17 \times 10^{-10}$) |

FIG. 7D

| TYPICAL ISO PROPERTIES | | | | | |
|---|---|---|---|---|---|
| MECHANICAL PROPERTY | TEMPERATURE | PRESSURE | ASTM METHOD | SI ENGLISH UNITS | TYPICAL PROPERTIES |
| TENSILE STRENGTH | 23°C (73F°)<br>260°C (500°F) | — | D-638<br>D-1708 SPECIMEN | MPa (kpsi) | 124 (18.0)<br>55 (8.0) |
| TENSILE ELONGATION | 23°C (73F°)<br>200°C (500°F) | — | D-638<br>D-1708 SPECIMEN | % | 4.3<br>13 |
| YOUNG'S MODULUS | 23°C (73F°)<br>260°C (500°F) | — | D-638<br>D-1708 SPECIMEN | MPa (kpsi) | 4,140 (600)<br>2,350 (340) |
| FLEXURAL STRENGTH | 23°C (73F°)<br>260°C (500°F) | — | D-790 | MPa (kpsi) | 200 (20)<br>96 (14) |
| FLEXURAL MODULUS | 23°C (73F°)<br>260°C (500°F) | | D-790 | MPa (kpsi) | 6,370 (923)<br>3,540 (514) |
| COMPRESSIVE STRENGTH | 23°C (73F°)<br>260°C (500°F) | — | D-695 | MPa (kpsi) | 386 (56)<br>450 (65) |
| COMPRESSIVE STRENGTH, ULTIMATE | 23°C (73F°)<br>260°C (500°F) | — | D-695 | MPa (kpsi) | 41<br>63 |
| COMPRESSIVE STRESS AT 10% STRAIN | 23°C (73F°)<br>260°C (500°F) | — | D-695 | MPa (kpsi) | 220 (31.9)<br>81 (11.7) |

FIG. 7G

| | | | | |
|---|---|---|---|---|
| DEFORMATION UNDER LOAD AFTER 24 HOURS | 23°C (73F°) | 14 MPa (2 kpsi) | D-621 | 0.05 |
| COMPRESSIVE CREEP<br>• 10 HOURS<br>• 100 HOURS<br>• 1000 HOURS | 23°C (73F°) | 10 MPa (1.5 kpsi) | D-2990 | %  0.02<br>0.02<br>0.05 |
| COMPRESSIVE CREEP<br>• 10 HOURS<br>• 100 HOURS<br>• 1000 HOURS | 23°C (73F°) | 14 MPa (2.5 kpsi) | D-2990 | %  0.03<br>0.05<br>0.07 |
| ROCKWELL "E" HARDNESS | — | — | D-785 | 91 |
| POISSON'S RATIO | 23°C (73F°)<br>260°C (500°F) | — | D-638 | 0.34<br>0.34 |

| | TEMPERATURE | PRESSURE | ASTM METHOD | SI ENGLISH UNITS | TYPICAL VALUES |
|---|---|---|---|---|---|
| THERMAL PROPERTY | | | | | |
| COEFFICIENT OF THERMAL EXPANSION<br>• PERPENDICULAR<br>• PARALLEL | 10 - 150°C<br>(122 - 302°F) | — | E-831 | m/m °C<br>OR m/m-K<br>(in/in °F) | $42.7 \times 10^{-6}$<br>$(23.7 \times 10^{-6})$ |
| THERMAL CONDUCTIVITY | 50°C (122F°)<br>100°C (212F°)<br>300°C (572F°) | — | F-433 | W/M-K<br>(Btu/hr-in°F) | 0.59 (0.03)<br>0.66 (0.03)<br>0.58 (0.03) |
| SPECIFIC HEAT | 60°C (140°F) | | E-1269 | J/kg °C (Btu/lb °F) | $9.2 \times 10^5$ (0.22) |
| WEAR PROPERTY | VELOCITY | PRESSURE | METHOD | SI ENGLISH UNITS | TYPICAL VALUES |
| COEFFICIENT OF FRICTION, UNLUBRICATED, AIR<br>• 0.88 (25K) PV<br>• 3.50 (100K) PV<br>• 10.50 (300K) PV | 0.7 m/s (134 fpm)<br>2.0 m/s (400 fpm)<br>3.0 m/s (585 fpm) | 1.3 MPa (187 psi)<br>1.7 MPa (250 psi)<br>3.5 MPa (500 psi) | FALEX | — | 0.25<br>0.07<br>0.11 |
| WEAR FACTOR, UNLUBRICATED, AIR<br>• 0.88 (25K) PV<br>• 3.50 (100K) PV<br>• 10.50 (300K) PV | 0.7 m/s (134 fpm)<br>2.0 m/s (400 fpm)<br>3.0 m/s (585 fpm) | 1.3 MPa (187 psi)<br>1.7 MPa (250 psi)<br>3.5 MPa (500 psi) | FALEX | mm-sec/MPa-m-hr<br>(in³-min/ft-lb-hr) | $1.7 \times 10^{-3} (24 \times 10^{-10})$<br>$0.8 \times 10^{-3} (11 \times 10^{-10})$<br>$1.2 \times 10^{-3} (17 \times 10^{-10})$ |
| OTHER PROPERTY | TEMPERATURE | TIME | ASTM METHOD | SI ENGLISH UNITS | TYPICAL VALUES |
| SPECIFIC GRAVITY | 23°C (73F°) | — | D-792 | | 1.50 |
| WATER ABSORPTION | 23°C (73F°) | 24 HOURS | D-570 | % WEIGHT CHANGE | 0.06 |

FIG. 7I

| | ASTM METHOD | UNITS | VESPEL SP | | | | | SCP-5000 UNFILLED | VESPEL SCP SCP-5094 GRAPHITE BEARING GRADE | SCP-5050 GRAPHITE BEARING GRADE |
| | | | SP-1 UNFILLED | SP-21 15% GRAPHITE | SP-22 40% GRAPHITE | SP-211 15% GRAPHITE 10% TEFLON | SP-3 VACUUM BEARING GRADE | | | |
|---|---|---|---|---|---|---|---|---|---|---|
| MECHANICAL | | | | | | | | | | |
| TENSILE STRENGTH, 73°F | D1708/D638 | kpsi | 12.5 | 9.5 | 7.5 | 6.5 | 8.2 | 23.6 | 18.0 | 10.5 |
| TENSILE STRENGTH, 500°F | D1708/D638 | kpsi | 6.0 | 5.5 | 3.4 | 3.5 | | 9 | 8.0 | 5.6 |
| ELONGATION AT BREAK, 73°F | D1708/D638 | % | 7.5 | 4.5 | 3.0 | 3.5 | 4.0 | 7.5 | 4.3 | 2.5 |
| ELONGATION AT BREAK, 500°F | D1708/D638 | % | 6.0 | 3.0 | 2.0 | 3.0 | | 49 | 13 | 5.3 |
| FLEXURAL MODULUS, 73°F | D790 | kpsi | 450 | 550 | 700 | 450 | 475 | 836 | 923 | 1,130 |
| FLEXURAL MODULUS, 500°F | D790 | kpsi | 250 | 370 | 400 | 200 | 270 | 436 | 514 | 740 |
| COMPRESSIVE STRESS AT 10% STRAIN, 73°F | D695 | kpsi | 19.3 | 19.3 | 16.3 | 14.8 | 18.5 | 33.4 | 31.9 | 25 |
| DEFORMATION UNDER 2,000 psi LOAD | D621 | % | 0.14 | 0.10 | 0.08 | 0.13 | 0.12 | .05 | .05 | 0.03 |
| FRICTION | | | | | | | | | | |
| COEFF. OF FRICTION AT PV = 25,000 psi-ft/min* | | | 0.29 | 0.24 | 0.20 | 0.12 | 0.25 | 0.26 | 0.25 | 0.12 |
| COEFF. OF FRICTION AT PV = 100,000 psi-ft/min* | | | | 0.12 | 0.09 | 0.08 | 0.17 | 0.15 | 0.07 | 0.08 |
| STATIC COEFF. OF FRICTION IN AIR* | | | 0.35 | 0.30 | 0.27 | 0.20 | | | | |
| PV LIMIT (UNLUBRICATED)** | | kpsi ft/min | | 350 | 350 | 100 | | | 500 | |
| OTHER PROPERTIES | | | | | | | | | | |
| COEFF. OF THERMAL EXPANSION, 73-500°F | D696 | 10⁻⁶ in/in °F | 30 | 27 | 21 | 30 | 29 | 26 | 24 | 16 |
| HARDNESS | D785 | ROCKE | 45-60 | 25-45 | 5-25 | 1-20 | 40-55 | 95 | 91 | 63 |
| WATER ABSORPTION, 24 HR AT 73°F, 100% RH | D570 | % | 0.24 | 0.19 | 0.14 | 0.21 | 0.23 | 0.08 | 0.06 | 0.04 |

* VESPEL CARBON STEEL, STEADY STATE, UNLUBRICATED, IN AIR, THRUST BEARING
** PV LIMITS FOR ANY MATERIAL VARY WITH DIFFERENT COMBINATIONS OF PRESSURE AND VELOCITY AS WELL AS OTHER CONDITIONS

| SOLVENT COMPATIBILITY MATERIALS TESTING NAME MATERIAL (DESCRIPTION OF MATERIAL) ||
|---|---|
| TEST # | SOLVENTS |
| 1 | AIR (CONTROL) |
| 2<br>7<br>10<br>20<br>23<br>24 | METHANOL + MILI-Q WATER (50:50)<br>100% METHANOL<br>100% THF (TETRAHYDROFURAN)<br>100% WATER (MILL-Q)<br>100% ACN (ACETONITRILE)<br>ACN + MILLI-Q WATER (50:50) |
| 3<br>8<br>12 | 0.2% FORMIC ACID IN MILLI-Q WATER<br>EDTA (ETHYLENEDIAMINETERACETIC ACID) 2mM<br>AMMONIUM HYDROXIDE (50mM) |
| 14<br>17<br>28<br>30 | PHOSPHATE BUFFER 12pH<br>AMMONIUM ACETATE (50mM)<br>PHOSPHATE BUFFER (10mM) pH2.5<br>PHOSPHATE BUFFER (10mM) pH9 |
| 31 | AMMONIUM BICARBONATE (10mM) |
| 32<br>33 | 0.2% FORMIC ACID IN ACETONITRILE<br>0.2% FORMIC ACID IN METHANOL (NANOACQUITY) |
| 36<br>37<br>38 | 1% ACETIC ACID IN MILLI-Q WATER (NANOACQUITY)<br>1% ACETIC ACID IN ACN (NANOACQUITY)<br>1% ACETIC ACID IN METHONAL (NANOACQUITY) |
| 39<br>40<br>41 | 1% FORMIC ACID IN ACETONITRILE AND WATER (FOR ICP-MS)<br>0.1% HCL IN MILLI-Q WATER (FOR ICP-MS) pH 0.6<br>0.1% HCL IN MILLI-Q WATER (FOR ICP-MS) pH 2.0 |

| | |
|---|---|
| 4 | 100% IPA (ISOPROPAL ALCHOHOL) |
| 6 | 100% METHYLENE CHLORIDE |
| 9 | ETHYL ACETATE |
| 16 | CHLORFORM |
| 18 | HEXANE |
| 19 | 100% TCB (TRICHLOROBENZENE) |
| 22 | 100% DMF (DIMETHYLFORMAMIDE) |
| 27 | 100% DMSO (DIMETHYL SULFOXIDE) |
| 5 | PHOSPHORIC ACID (50%) |
| 13 | SULFURIC ACID (20mM) IN MILLI-Q WATER |
| 15 | NITRIC ACID (6M) IN MILLI-Q WATER |
| 26 | SODIUM HYDROXIDE (1M) IN MILI-Q WATER pH14 |
| 29 | WEXIDE (5oz/1gal H20) |
| 11 | 0.1% TFA (TRIFLUOROACETIC ACID) IN MILLI-Q WATER |
| 21 | 0.1% TEA (TRIETHYLAMINE) IN MILLI-Q WATER |
| 25 | 0.1% HFBA (HEPTAFLUOROBUTYRIC ACID) IN MILLI-Q WATER |
| 34 | 0.1% TFA (TRIFLUOROACETIC ACID) IN ACENITRILE (NANOACQUITY) |
| 35 | 0.1% TFA (TRIFLUOROACETIC ACID) IN METHANOL (NANOACQUITY) |

FIG. 9B

| TEST # | 14 BIOCOMPATIBILITY MATERIALS TESTING NAME (DESCRIPTION OF MATERIAL) SOLVENTS |
|---|---|
| 1 | AIR (CONTROL) |
| 2 | 100% MILLI-Q (OR EQUIVALENT 18 Mohm) WATER |
| 3 | 100% HPLC GRADE (OR EQUIVALENT) METHANOL |
| 4 | 100% HPLC GRADE (OR EQUIVALENT) ACETONITRILE |
| 5 | 0.2% TRIFLUOROACETIC ACID (TFA) IN MILLI-Q (OR EQUIVALENT) WATER |
| 6 | 0.2% TRIFLUOROACETIC ACID (TFA) IN ACETONITRILE |
| 7 | 0.1 M TRIETHYLAMMONIUM ACETATE IN MILLI-Q WATER, pH ADJUSTED TO 7.0 |
| 8 | 15mM TRIETHYLAMINE/400mM HEXAFLUORO ISOPROPANOL IN MILLI-Q WATER AT A pH OF 7.9 |
| 9 | 10mM SODIUM PHOSPHATE/1M SODIUM CHLORIDE IN MILLI-Q WATER, pH ADJUSTED TO 6.0 |
| 10 | 0.1 M SODIUM PHOSPHATE/0.1M SODIUM SULFATE/0.05% SODIUM AZIDE IN MILLI-Q WATER AT A pH 6.7 |
| 11 | 50mM AMMONIUM FORMATE IN MILLI-Q WATER, pH ADJUSTED TO 4.4 |
| 12 | 0.1M SODIUM PHOSPHATE (DIBASIC)/1M SODIUM CHLORIDE IN MILLI-Q WATER, pH ADJUSTED TO 2.0 |
| 13 | 0.1M SODIUM HYDROXIDE/0.5 SODIUM ACETATE IN MILLI-Q WATER, CONFIRM pH ABOVE 12.0 |
| 14 | 6mM HCl IN MILLI-Q WATER |

FIG. 9C

STATIC AND DYNAMIC SEALS

RELATED APPLICATION

This application is a National Stage of International Application No. PCT/US2011/20745, filed Jan. 11, 2011, which claims priority to U.S. Provisional Application No. 61/293,879, filed Jan. 11, 2010, which are hereby incorporated by reference.

BACKGROUND

1. Technical Field

This application generally relates to seals, and more particularly to materials used with components having surfaces forming static and/or dynamic seals.

2. Description of Related Art

Samples may be processed in a laboratory or other environment for a variety of different purposes and applications. Chromatography refers to techniques for separating sample mixtures. Common chromatographic techniques include gas chromatography (GC) and liquid chromatography (LC). With an instrument that performs LC, a liquid sample to be analyzed is introduced in small volumes for analysis. The sample may be injected into a solvent stream which is carried through a column. The compounds in the sample can then be separated by traveling at different speeds through the column resulting in the different compounds eluting from the column at different times. In connection with High Performance Liquid Chromatography (HPLC) and Ultra Performance Liquid Chromatography (UPLC), pressure is used to facilitate fluid flow in the system through the chromatographic column.

An instrument that performs LC or GC includes different components that may be fabricated using a variety of different materials. In connection with systems such as an LC system, a variety of different components may form seals operating under pressure. A component or part, such as a rotor, having a surface used in forming a seal may be replaced, for example, when there is excessive leakage so that a desired pressure cannot be adequately maintained. In such a case, the component or part may be characterized as having reached the end of its useful lifetime. The selection of material(s) used in forming the components, and surfaces thereof where seals are formed, may affect the lifetime, or amount of time, the component may be used in an LC or other system prior to replacement. The material(s) selected may have particular characteristics or properties dependent on the application and use within a system.

SUMMARY OF THE INVENTION

In accordance with one aspect of the invention is a sealing member forming a static seal or a dynamic seal at a surface thereof, the sealing member having at least the surface thereof formed from one of VESPEL®SCP 5000 material or VESPEL®SCP 50094 material. The sealing member may form a static seal or a dynamic seal in a liquid chromatography system. The sealing member may be included in a valve. The valve may be an injection valve. The sealing member may be a rotor element. The sealing member may be a needle seal. The needle seal may include a first portion formed from VESPEL® SCP 5000 material, the first portion including a through hole where sidewalls in the through hole form the surface in contact with a needle tip forming a dynamic seal. The needle seal may include a second portion encasing the first portion. The second portion may be formed from materials including gold or stainless steel. The through hole may include a first portion which tapers inwardly with respect to an opening at a first end of the through hole into which a needle having the needle tip is inserted. The through hole may include a second portion adjacent to the first portion of the needle seal which is untapered. The through hole may include another tapered portion adjacent to the second portion of the needle seal. The other tapered portion of the needle seal may form a conical portion at a second end of the through hole opposing the first end. The first portion of the needle seal may include a top portion and a bottom portion having a t-shaped profile. The top portion may have a cylindrical shape and said bottom portion may be inserted into a second portion of the needle seal. The second portion of the needle seal may be formed from stainless steel. The second portion of the needle seal may be formed from a material having mechanical properties indicating that the second portion of the needle seal has a mechanical strength which is greater than the first portion.

In accordance with another aspect of the invention is a needle seal forming a seal at a surface thereof, wherein at least the surface is formed from materials including one of VESPEL® SCP 5000 material or VESPEL® SCP 50094 material. The seal formed may be a dynamic seal in a liquid chromatography system. The needle seal may be included in an injector used to inject a sample into the liquid chromatography system. The needle seal may include a first inner portion made of VESPEL® SCP 5000 material with a through hole formed therethrough. An inner surface of the through hole may be the surface at which a dynamic seal is formed when the inner surface is in contact with a needle tip inserted into the through hole. The needle seal may include a second portion encasing the first inner portion. The second portion may comprise one of gold or stainless steel. The needle seal may include a first portion having a t-shaped profile and may be made of VESPEL® SCP 5000 material with a through hole formed therethrough. An inner surface of the through hole may be the surface at which a dynamic seal is formed when the inner surface is in contact with a needle tip inserted into the through hole. The first portion may include a top portion and a bottom portion. The top portion may have a cylindrical shape and the bottom portion may be inserted into a second portion. The second portion may be formed from stainless steel. The second portion may be formed from a material having mechanical properties indicating that the second portion has a mechanical strength which is greater than the first portion.

In accordance with another aspect of the invention is a rotor element forming a seal at a surface thereof and having at least the surface thereof formed from materials including one of VESPEL®SCP 5000 material or VESPEL® SCP 50094 material. The rotor element may be included in a valve. The valve may be an injection valve. The valve may be included in a system that performs liquid chromatography.

In accordance with another aspect of the invention is a method of fabricating a part comprising providing a portion of a material, said material being one of VESPEL® SCP 5000 material or VESPEL®SCP50094 material; and processing the portion to produce the part. The part is used in forming a static seal or a dynamic seal at a surface thereof. The processing may include at least one of machining said portion, cutting said portion, and press-fitting said portion.

In accordance with another aspect of the invention is a method of fabricating a rotor comprising providing a portion of a material having a disk-like shape, the material being one of VESPEL® SCP 5000 material or VESPEL® SCP50094 material; and patterning at least a first surface of the portion to have at least one groove formed thereon. The method may also include cutting the portion from a cylindrical rod made of said material.

In accordance with another aspect of the invention is a method of fabricating a needle seal comprising providing a portion of a material, said material being one of VESPEL® SCP 5000 material or VESPEL® SCP50094 material; and processing the portion to produce the needle seal. The processing includes forming a through hole through the portion and the through hole has an opening at one end to a first inwardly tapered portion of the through hole. The processing may include at least one of press-fitting and machining.

BRIEF DESCRIPTION OF THE DRAWINGS

Features and advantages of the present invention will become more apparent from the following detailed description of exemplary embodiments thereof taken in conjunction with the accompanying drawings in which:

FIGS. 2A and 2B illustrate examples of a needle and an embodiment of a needle seal in accordance with techniques described herein;

FIGS. 2C-2I, and 3A-3R are examples illustrating various aspects of needle seal embodiments in accordance with techniques herein;

FIG. 5A-5I, 6A-6G are illustrations of various properties of VESPEL® SCP 5000 material as may be used in an embodiment in connection with techniques herein;

FIGS. 7A-7I and FIGS. 8A-8C are illustrations of various properties of VESPEL® SCP 50094 material as may be used in an embodiment in connection with techniques herein;

FIGS. 8D-8F are illustrations of various properties of VESPEL® SCP 5000 material and VESPEL® SCP 50094 material as may be used in an embodiment in connection with techniques herein; and FIGS. 9A, 9B and 9C are examples illustrating results of chemical compatibility tests using samples of SCP 5000 material as may be used in an embodiment in connection with techniques herein.

DETAILED DESCRIPTION OF EMBODIMENT(S)

Figure 1A:
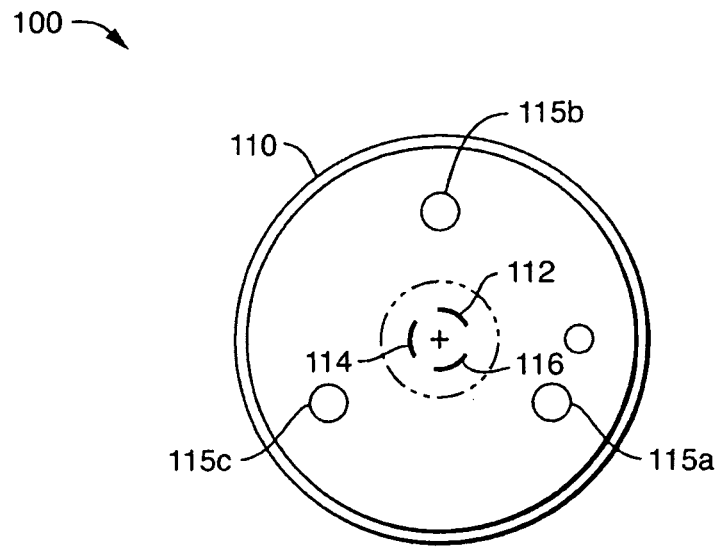
FIGS. 1A and 1B are examples illustrating an embodiment of a rotor made in accordance with the techniques described herein.

Described in following paragraphs are techniques that may be used in fabricating components of a system such as a liquid chromatography (LC) system. The LC system may be, for example, a High Performance Liquid Chromatography (HPLC) or an Ultra Performance Liquid Chromatography (UPLC) system such as the ACQUITY UPLC® and nanoACQUITY UPLC® systems from Waters Corporation of Milford Mass. An LC system such as the foregoing from Waters Corporation may operate under high pressure such as in the range of 5000 PSI (e.g, exemplary for some HPLC systems) to 15000 PSI (exemplary for some UPLC systems). An LC system may include components fabricated using a variety of different techniques and materials. In one embodiment of an LC system, one or more components used in forming a seal may be made of VESPEL® SCP 5000 material or SCP 50094 material as sold by DuPont™. VESPEL® SCP 5000 material may be characterized as an unfilled thermoset polyimide polymer. VESPEL® SCP 50094 material may be characterized as a thermoset polyimide polymer with a graphite filler. Additional properties and characteristics of the foregoing materials are described in more detail in following paragraphs and figures.

It will be appreciated by those skilled in the art that the material referred to herein by a particular commercial name and/or being provided by a particular vendor or manufacturer may also be referred to using other names and/or be provided by other vendors than as described herein.

The seal formed using a component, such as a component made of VESPEL® SCP 5000 material or SCP 50094 material as sold by DuPont™, may be a static or a dynamic seal. A dynamic seal may be defined as a seal where there is relative movement between the surfaces forming the seal. In contrast to a dynamic seal is a static seal where there is no relative movement between surfaces forming the seal. Described herein are examples of components that may be included in an LC system where the components are used in forming a seal, such as a dynamic seal. However, it will be appreciated by those skilled in the art that use of the materials and techniques described herein are not limited to those particular examples provided for illustration.

An LC system may include an injector used to inject controlled volumes of a sample, either manually or automatically, into a fluid stream which carries the sample to an LC column where the sample may then be separated. The injector may include an injector valve used in connection with controlling or regulating the introduction of fixed volumes of a sample for analysis in the LC system. The injector valve may include one or more parts each having a pattern formed on a surface of the part. The pattern may include, for example, one or more grooves. The surface upon which the grooves are formed may also be in contact with the fluid containing the sample. That is, the groove or other patterned area may form part of the flow path of the sample in the LC system.

As described in following paragraphs, one or more parts of an injector valve assembly may be fabricated using the material described herein. As will be appreciated by those skilled in the art, an injector valve assembly may include other parts and may have additional detail than as described herein for purposes of illustrating the techniques herein. Injector valve assemblies, for example, as described in WO 2005/079543 A2 (PCT/US2005/005714) PIN VALVE ASSEMBLY, Keene et al., which is incorporated by reference herein, are generally known in the art. A valve, such as an injector valve that may be used in an LC system, may include a stator and a rotor acting together to connect or align ports of the valve. The rotor may be actuated in a rotational manner relative to the axis of the valve in order to vary the position of the rotor relative to the stator, which remains stationary. A first surface of the rotor may face a surface of the stator. The rotor may be a removable disk which, as will be described in following paragraphs, may include a pattern formed on the first surface. The rotor may be included in a valve assembly including a drive shaft coupled to another component, such as an engine or motor, to facilitate actuating the valve assembly such as in connection with loading a volume of sample.

What will now be described is a rotor having a pattern formed on a surface thereof. The rotor may be made of VESPEL® SCP 5000 material or SCP 50094 material and may be included in an injector valve of an LC system.

It should be noted that exemplary measurements are included in connection with figures herein. The measurements provided in following figures are approximate values and in inches unless otherwise indicated such as those angular degree measurements. The measurements indicated are only examples of what may be included in an embodiment for purposes of illustration and should not be construed as a limitation of techniques herein.

Figure 1B:
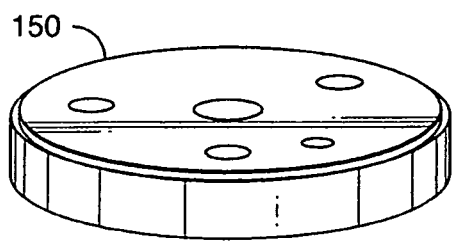

Referring to FIGS. 1A and 1B, shown are illustrations of an embodiment of a rotor that may be patterned in accordance with techniques described herein. The rotor of FIGS. 1A and 1B may be included in an injector valve assembly. The rotor having various views set forth in the example 100 of FIGS. 1A and 1B may include grooves 112, 114 and 116 on a surface thereof. Element 110 provides a surface view of the rotor facing the stator. The rotor in 110 is illustrated as a disk having 3 grooves 112, 114, and 116 formed on the surface thereof facing the stator. Elements 115a-c are 3 through holes that may be formed in the rotor. The through holes 115a-c may be used to position the rotor in the valve assembly. For example, another part (not shown) included in the valve assembly and in contact with a surface of the rotor not facing the stator may include 3 protrusions with positions corresponding to each of the 3 through holes 115a-c.

In one example embodiment of a rotor, the rotor may have a diameter measuring approximately 0.706+/−0.003 inches. Each of the grooves may have approximately the same size and dimensions. For example, each of the grooves may be 0.008+/0.001 inches in width and hold a volume of 0.04 microliters. Each of the grooves 112, 114, and 116 are located a same distance R from the center of the rotor and are shaped to extend along a portion of a same circumference of a circle having radius R. In this example, the foregoing circle has an exemplary diameter of 0.100 inches. Each groove has a sufficient length to extend about a portion of the circumference associated with a 60 degree angle. Each groove is positioned to be equidistant from the other grooves along the circumference. Element 150 shows a different view of the rotor as a disk included in an outer metal ring such as may be included in an injector valve. The 3 grooves 112, 114 and 116 as well as the through holes 115a-c may be formed using any one or more suitable technique known in the art such as, for example, by machining using a drill or other appropriate tool.

A stator (not illustrated) may be included in an injection valve assembly with the rotor of FIGS. 1A and 1B. As known in the art and also described in more detail below, the stator may have a first surface which is not in contact with a surface of the rotor and a second opposing surface which is in contact with the rotor surface having grooves formed therein such as illustrated in the example 100 of FIGS. 1A and 1B. The foregoing first surface of the stator may include a number of ports, such as 6 ports having corresponding port holes through the stator with openings on the second surface. The openings of port holes formed on the second surface of the stator facing the rotor are located a same distance from the center as the 3 grooves 112, 114, and 116 in the rotor 110 of FIG. 1A. The foregoing provides for the openings of the port holes on the second stator surface (in contact with the rotor) being in alignment with the rotor grooves 112, 114 and 116.

The rotor is a disk having 3 grooves formed therein in this exemplary valve assembly although the rotor formed using the techniques described herein may have grooves formed therein of any number, shape and size. For example, in a second embodiment of the rotor made in accordance with techniques described herein, the rotor may include 3 grooves where grooves 114 and 116 may be of a same size and have dimensions as described above. The third groove 112 may have a longer length than grooves 114, 116. Groove 112 may have a sufficient length to extend about a portion of the foregoing circumference associated with a 74 degree angle rather than a 60 degree angle.

An embodiment of a rotor formed from VESPEL® SCP 5000 material may be made, for example, by cutting a disk portion of a desired thickness, such as 0.141 inches, from a cylindrical rod of the VESPEL® SCP 5000 material. The disk portion may be further shaped in accordance with desired specifications using any suitable techniques known to one of ordinary skill in the art. For example, grooves, through holes, and the like, may be made using machining or other suitable techniques known in the art. As another example, the grooves or patterns such as on the surface of a rotor as described herein may be formed using an embossing technique by applying pressure, alone or in combination with heat, such as described in U.S. Provisional Patent Application No. 61/108,965, filed on Oct. 28, 2008, TECHNIQUES FOR PATTERNING VALVE COMPONENTS, which is incorporated by reference herein, and the like. Additionally, any portion of the rotor may be optionally coated as desired using a known coating and appropriate technique. An embodiment of a rotor formed from VESPEL® SCP 50094 material may also be made in a manner similar to that as described above.

An embodiment of the rotor such as described above actuates in a rotational fashion about its center axis. The actuation causes the grooves located on the rotor surface facing the stator to move providing different fluidic connections to different ports of the stator where a groove forms a channel between two ports through which fluid flows. Additionally, tubes may be connected to ports of the stator in the first surface (not facing the rotor) in connection with forming a fluid path of an injected sample into and out of a sample loop. The sample may be forced out of the sample loop by applying pressure such as using a pump. Any of the ports may be inlet or outlet ports with respect to fluid in the LC system depending on the valve configuration and use. In an injector valve of an LC system, the rotor may be actuated to different positions relative to a stationary stator in order to load and then inject volumes of a sample into the LC system. It should be noted that the rotor and associated valve as described herein in connection with an injector in an LC system may be used in a fixed loop or other type of injector. Also, the rotor and materials as described herein may be used in connection with valves other than those used in connection with an injector.

The foregoing is an example of a type of an injector, also known as a fixed loop injector, as may be included in an LC system where the sample is transported into the sample loop and the sample loop becomes part of the system flow path. For example, the ACQUITY UPLC® system from Waters Corporation uses a fixed loop injector. Another type of injector known in the art may be characterized as a direct injector where a sample may be aspirated into a needle and the needle becomes part of the system flow path. In the direct injector, there is no sample loop utilized in connection with sample introduction into the LC system. For example, the Alliance HPLC® System by Waters Corporation uses direct injection.

What will now be described are exemplary embodiments of a sealing member, which is a needle seal, used in a direct injector. In such an embodiment, the needle seal may be formed using one of the materials described herein, such as VESPEL® SCP 5000 material or SCP 50094 material. It should be noted that the term sealing member may be used to generally refer to a part such as a needle seal or rotor described herein used in forming a static or dynamic seal.

Figure 2E:
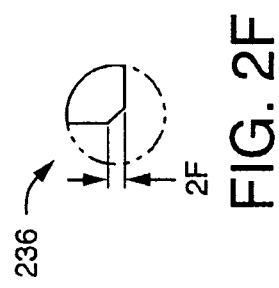

Referring to FIGS. 2A and 2B, shown is an example of a needle seal, needle, and components of an injection port for use with direct injection in an LC system in accordance with techniques herein. The example 180 illustrates components of an injection port 181 including a needle seal 184. Exemplary embodiments of the needle seal in accordance with techniques and materials herein are described in more detail in following paragraphs. The needle seal 184 may be characterized as forming a dynamic seal during operation of a direct injection technique to introduce a sample into the LC system. In connection with performing direct injection, a sample may be aspirated into a needle, such as illustrated by 196. At a first point in time, the needle is then inserted into opening 182 with a sufficient downward force in the vertical direction into passageway 183 and into an opening 184a in the needle seal 184. The needle tip comes into contact with sidewalls within the opening 184a in the needle seal 184 to form a seal. Element 190 shows an enlarged view of a portion of the needle seal included in 181. As illustrated in further detail in 190, the opening 184a forms a throughhole through the needle seal. The inner sidewalls of 184a are tapered and narrowed to a point so that the needle tip, when inserted into 184a, comes into contact with the inner sidewalls of 184a as it narrows. It is at the foregoing points of contact between the needle tip and inner sidewalls that the seal is formed. At the first point in time during which the needle is inserted, there is no pressurization with respect to the needle seal. Once the needle is inserted into the needle seal 184 and an appropriate amount of force is present at the point of contact between the needle tip and needle seal sidewall surfaces within the opening 184a, fluid flow is turned on resulting in pressurization of the system. A seal is formed at the point of contact between the needle tip and inner sidewalls of 184a. The fluid flow through the needle is then stopped and the needle seal and system are still pressurized. At a second point in time, the needle is then pulled in the upward vertical direction along 183 out of the needle seal 184 causing depressurization.

As described in more detail in U.S. Provisional Patent Application No. 61/293,902, filed on Jan. 11, 2010, INJECTION PORT NEEDLE SUPPORT AND WASHING, which is incorporated by reference herein (the "NEEDLE SUPPORT AND WASHING patent application"), the material denoted by 187, the passageway 183 formed therein, and optionally ports 186a, 186b and their respective connections 186c, 186d to 183 may comprise a needle support structure. Passageway 183 may have a diameter, for example, within the range of 0.062+/−0.003 inches for use with the needle 196. It should be noted that the needle support structure may have other suitable dimensions to accommodate desired needle diameters and/or lengths that may be used in an embodiment.

In one embodiment, a needle 196 may be used which has a tapered tip so that the needle tip at a first point 196a has an outer diameter (OD) of 0.0.40+/−0.001 inches. The needle may be, for example, stainless steel. The needle tip may be tapered and narrowed from the first point 196a to the second point 196b where the outer surface of the needle tip comes into contact with the inner sidewalls of the needle seal. In one embodiment, the OD at the second point may be 0.013+/−0.001 inches. The needle tip may be tapered at a 13 degree angle as illustrated in 196. Element 190 illustrates some exemplary measurements in one embodiment of a needle seal 184 that may be used with the foregoing needle 196. The needle seal opening 184a may be narrowed as illustrated by tapering in accordance with the 20 degree angle to point 190a. From point 190a to point 190b the opening 184a may have a relatively uniform or constant diameter of 0.007 inches. The opening 184a may form a through hole through the needle seal 184 so that the needle enters at a first or top surface. Point 190b may be at a bottom surface of the needle seal opposing the foregoing top surface.

Also illustrated are ports 186a and 186b through which different solvents or other fluids may flow into/out of 181. Element 185 may be a port and associated conduit or tubing through which the sample flows out of once injected as described above. Element 185 may be connected, directly or indirectly, to an LC column. The amount of force applied and used in connection with the needle seal and inserted needle may be determined using any of a variety of techniques known in the art. For example, the needle seal embodiments described herein forming a dynamic seal in connection with direct injection may be used with the techniques described, for example, in U.S. Provisional Patent Application No. 61/293,889, filed on Jan. 11, 2010, NEEDLE SEAL FORCE SENSOR, (the "NEEDLE SEAL FORCE SENSOR patent application") which is incorporated by reference herein. Some components illustrated in FIG. 2B, such as the spring 188a and load cell 188b, may be optionally included in an embodiment which uses a force sensor as described in the NEEDLE SEAL FORCE SENSOR patent application.

Referring to FIGS. 2C-2I, shown is an example of a first embodiment of a needle seal that may be made in accordance with techniques described herein. The example 200 illustrates a needle seal 220 having a first inner portion or core 224 and a second outer portion or core 222. Formed in the first inner portion 224 is opening 226 (referenced as 184a in FIGS. 2A and 2B) into which a needle is inserted for direct sample injection. In this embodiment, the inner portion 224 may be made of VESPEL® SCP 5000 material. The inner portion 224 may be encased within the second outer portion 222. The second outer portion 222 may be made, for example, of 18K or 24K gold or stainless steel. Element 210 shows a view of the needle seal 220 from the top. The diameter of the top of the needle seal of 210 may be 0.215 inches.

Figure 2F:
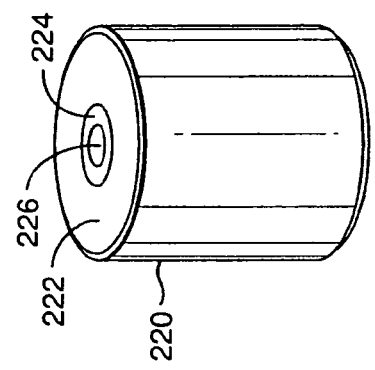
Figure 2C:
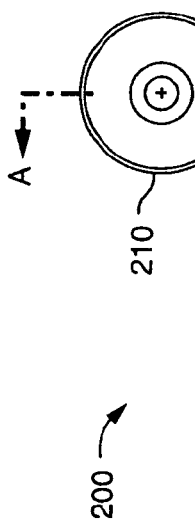
Figure 2D:
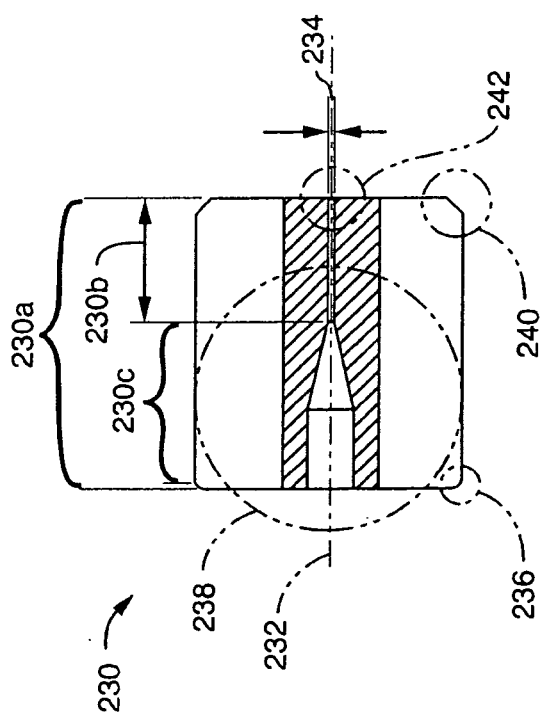

Element 230 shows a side or lateral view of the needle seal taken along line A-A of 210. In the example 230, the length 230a of the needle seal outer cylindrical walls may be 0.235+/0.003 inches. As described above, the opening 232 may form a through hole through the needle seal having a first portion 230c and a second portion 230b. The portion 230b may be untapered and may have a length of 0.093 inches. The opening 234 may have a diameter of 0.007+0.001/−002 inches. Additional details of various aspects of 230 are provided in subsequent figures denoted as detail B 236, detail C 238, detail F 240, and detail G 242. Element 236 of FIG. 2F illustrates additional detail B and indicates that a corner surface may be formed at the indicated 45 degree angle measuring 0.005+/−0.002 inches in length at the surface 2F.

Figure 2G:
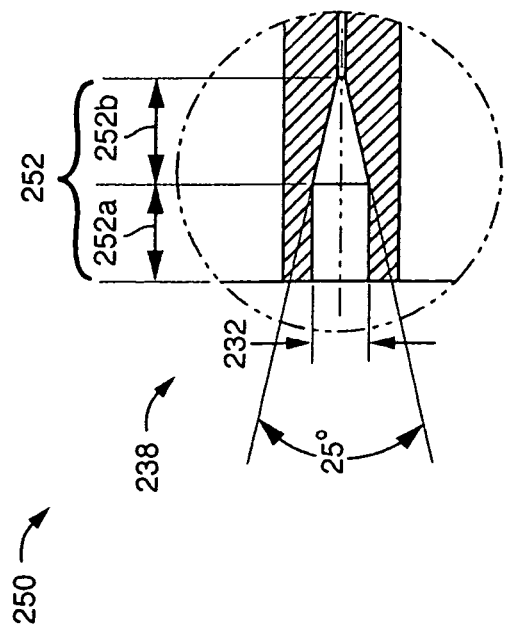
Figure 2H:
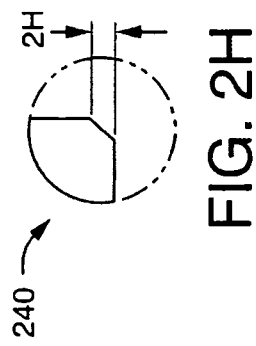
Figure 2I:
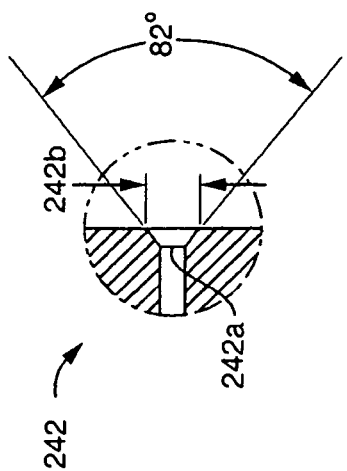

Referring to FIGS. 2G-2I, shown are additional details of various aspects of an embodiment of the needle seal in accordance with techniques herein as illustrated in FIG. 2C-2F. Element 238 provides additional detail C of the opening and through hole of the needle seal where the needle is inserted in connection with sample introduction into the LC system. The portion 252 includes a first portion 252a which has a uniform diameter and a second portion 252b which is a narrowed tapered portion. The first portion 252a may have a length of 0.065 inches and the second portion 252b may have a length of 0.077 inches. The opening 232 at a surface of the needle seal where the needle is first inserted may have a diameter of 0.0410+0.0005/−0.0010 inches. The second tapered portion may form a conical section having a 25 degree angle as illustrated. Element 240 provides additional detail F and indicates that a corner surface formed at the indicated 45 degree angle may be 0.013+0.010/−0.005 inches in length measured at a surface 2H. Element 242 provides additional detail G and indicates that the through hole at the bottom surface of the seal may be outwardly tapered at an 82 degree angle as illustrated. As measured at the bottom surface at point 242b, the through hole may have a diameter of 0.015+/−0.003 inches. In 242, the through hole has a first diameter, such as 0.007 inches as described above, at point 242a which increases with respect to a second diameter of 0.015+/−0.003 inches as measured at the surface at point 242b thereby forming an outwardly tapered or conical section at the opening.

The needle seal embodiment illustrated in connection with FIGS. 2C-2I may be made by forming the inner portion or core (e.g., 224 of FIG. 2E) of VESPEL® SCP 5000 material. In one embodiment as described above with the rotor, the VESPEL® SCP 5000 material may be obtained in cylindrical rods where a disk portion may be cut at a desired thickness. The disk portion may then be further machined to obtain the desired shape and dimensions including the through hole with opening into which the needle is inserted. The outer portion or core (e.g., 222 of FIG. 2E), such as may be made from gold or stainless steel, may be formed to the desired shape and dimensions and may include a throughhole of an appropriate size to accommodate insertion of the inner portion or core of VESPEL® SCP 5000 material. The inner portion or core of VESPEL® SCP 5000 material is deformable so that the inner portion may be pressure fitted via insertion into the outer portion.

Referring to FIGS. 3A-3G, shown is an example of a second embodiment of a needle seal that may be made in accordance with techniques described herein. The example 300 illustrates a needle seal 320 having a portion or core 322. Formed in the portion 322 is opening 326 (referenced as 184a in FIGS. 2A and 2B) into which a needle is inserted for direct sample injection. In this embodiment, the portion 322 may be made of VESPEL® SCP 5000 material. Element 310 shows view of the needle seal 220 from the top. The diameter of the top of the needle seal in 310 may be 0.215+0.0005/−0.0010 inches.

Element 330 shows a side or lateral view of the needle seal taken along line A-A of 310. In the example 330, the length 330a of the needle seal outer cylindrical walls may be 0.235+/0.003 inches. As described above, the opening 332 may form a through hole through the needle seal having a first portion 330c and a second portion 330b. The portion 330b may be untapered and may have a length of 0.93 inches. The opening 334 may have a diameter of 0.007+ 0.001/−002 inches. Additional details of various aspects of 330 are provided in subsequent figures denoted as detail B 336, detail C 338, detail D 340, and detail E 242. Element 338 of FIG. 3D illustrates additional detail C and indicates that a corner surface 3D formed at the indicated 45 degree angle may be 0.005+/−0.002 inches.

Referring to FIG. 3E-3G, shown are additional details of various aspects of an embodiment of the needle seal in accordance with techniques herein as illustrated in FIGS. 3A-3D. Element 336 provides additional detail B of the opening and through hole of the needle seal where the needle is inserted in connection with sample introduction into the LC system. The portion 352 includes a first portion 352a which has a uniform diameter and a second portion 352b which is a narrowed tapered portion. The first portion 352a may have a length of 0.065 inches and the second portion 352b may have a length of 0.077 inches. The opening 332 at a surface of the needle seal where the needle is first inserted may have a diameter of 0.0410+/−0.0010 inches. The second tapered portion may form a 25 degree angle as illustrated. Element 342 provides additional detail E and illustrates that a corner surface 3F formed at the indicated 45 degree angle may be 0.013+0.010/−0.005 inches. Element 340 provides additional detail D and indicates that the through hole at the bottom surface of the seal may be outwardly tapered at a 90 degree angle as illustrated. As measured at the bottom surface at point 342b, the through hole may have a diameter of 0.015+/−0.003 inches. In 340, the through hole has a first diameter, such as 0.007 inches as described above, at point 342a which increases with respect to a second diameter of 0.015+/−0.003 inches as measured at the surface at point 342b thereby forming an outwardly tapered or conical opening.

The needle seal embodiment illustrated in connection with FIGS. 3A-3G may be made by forming the portion or core (e.g., 322 of FIG. 3C) of VESPEL® SCP 5000 material. In one embodiment as described above with the rotor, VESPEL® SCP 5000 material may be obtained in cylindrical rods where a disk portion may be cut at a desired thickness. The disk portion may then be further machined to obtain the desired shape and dimensions including the through hole with opening into which the needle is inserted. In this second embodiment of FIGS. 3A-3G, the entire needle seal may be formed from VESPEL® SCP 5000 material. The foregoing embodiment of FIGS. 3A-3G is in contrast to the first embodiment (FIGS. 2C-2I) of the needle seal where the VESPEL® SCP 5000 material forms an inner portion which is encased in an outer portion, such as made of gold or stainless steel.

Referring to FIGS. 3H-3R, shown is an example of a third embodiment of a needle seal that may be made in accordance with techniques described herein. The example 1000 illustrates a needle seal 1001 having a first part 1002 and a second part 1004. Formed in the second part 1004 is opening 1006 into which a needle is inserted for direct sample injection. In this embodiment, the second part 1004 may be made of VESPEL® SCP 5000 material. The first part 1002 may be made, for example, of stainless steel, such as type 316 stainless steel. The first part 1002 may more generally be made of one or more other materials which may be characterized as mechanically stronger than the material(s) comprising the second part 1004. For example, the first part 1002 may be made of a first material having one or more mechanical properties indicating that the first material (and resulting first part 1002) has a strength which is greater than the second part 1004.

The second part 1004 may include a top portion 1022a visible in the view of 1001 and a bottom portion 1022b which (as illustrated by the dashed lines) is not visible in the assembled view of 1001. The top portion 1022a has a circular or disk shape in the view of 1001. The dashed lines illustrate the outline formed by the bottom portion 1022b where the bottom portion 1022b is encased within sidewalls of the first part 1002. The first part 1002 has a hole or opening (not shown) into which the bottom portion 1022b is inserted when the needle seal is assembled.

As illustrated by 1022, the second part 1004 may have a T-shaped profile when viewed from a side or laterally and may have a length L1 of 0.235 inches. The diameter D1 of the bottom portion 1022b may have a size within the inclusive range of 0.1005 inches to 0.1010 inches. The length or thickness L2 of the top portion 1022a may be 0.055 inches. Element 1010 shows a view of the needle seal of 1001 from the top and the diameter of the top portion 1022a may be within the inclusive range of 0.225 to 0.226 inches.

Element 1021 shows a side or lateral view of the needle seal taken along line H-H of 1010 providing additional detail regarding the first part 1002 into which the bottom portion 1022b is inserted in the assembled needle seal of 1001. The first part 1002 may be cylindrical in shape having sidewalls 1002a with a hole or opening 1021a formed therethrough into which the bottom portion 1022b is inserted. The hole 1021a may have a diameter within the inclusive range of 0.1000 inches to 0.1004 inches. The sidewalls 1002a of the first part 1002 may have a length L3 of 0.180 inches. Element 1020 of FIG. 3L illustrates additional detail J and indicates that a corner surface 3L may be formed at the indicated 45 degree angle measuring 0.010+/−0.005 inches in length at the surface.

Referring to FIGS. 3M-O, shown are additional details of various aspects of the third embodiment of the needle seal in accordance with techniques herein. Element 1110 shows a side or lateral view of the needle seal taken along line A-A of 1010. In the example 1110, the length 1116 of the needle seal outer cylindrical walls (when assembled as illustrated in 1001) may be 0.235+/0.003 inches. The second part 1004 may have a hole or passage 1120 formed therethrough with openings 1006 and 1112, respectively, at opposite ends. The hole 1120 in the second part 1004 may be formed having a first portion 1119 (which is inwardly narrowed or tapered) and a second portion 1118. The portion 1118 may have a length of 0.156 inches. The opening 1122 may have a diameter of 0.007+0.001/−002 inches. The diameter 1114 of the first part at the bottom (end having opening 1122) may be in the inclusive range of 0.215 to 0.216 inches. Additional details of various aspects of 1110 are provided in subsequent illustrations denoted as detail B 1104, detail C 1102, detail F 1108, detail G 1124, and detail K 1106.

Element 1102 provides additional detail C of the opening 1106 of the needle seal where the needle is inserted in connection with sample introduction into the LC system. The portion 1119 is a narrowed tapered portion having a length of 0.079 inches. The opening 1006 at a surface of the needle seal where the needle is first inserted may have a diameter of 0.042+/−0.002 inches. The portion 1119 may form a conical section having a 25 degree angle as illustrated. The hole 1120 (and openings at opposite ends thereof) may be machined after the needle seal is assembled (e.g., as in 1001 of FIG. 3I). Element 1124 provides additional detail G and indicates that the through hole 1120 having opening 1122 at the bottom surface of the seal (opposite end of 1120 where the needle is inserted) may be outwardly tapered at a 90 degree angle as illustrated. As measured at the bottom surface at 1160, the through hole may have a diameter of 0.013+0.002/−0.001 inches. In 1124, the opening at the illustrated end of the through hole has a first diameter, such as 0.007+0.001/−002 inches as described above, at point 1161, which increases with respect to a second diameter of 0.013+0.002/−0.001 inches as measured at the surface at point 1160 thereby forming an outwardly tapered or conical section.

Referring to FIGS. 3P-3R, shown are additional details of various aspects of the third embodiment of the needle seal in accordance with techniques herein. The illustration 1200 of FIGS. 3P-3R further describes detail B 1104, detail F 1108 and detail K 1106 of FIG. 3M. Element 1106 provides additional detail K and indicates that a corner surface formed at the indicated 45 degree angle may be 0.005 inches in length measured at a surface 3Q. Element 1108 provides additional detail F and indicates that a corner surface formed at the indicated 45 degree angle may be 0.013+0.010/−0.005 inches in length measured at a surface 3P. Element 1104 of FIG. 3R illustrates additional detail B and indicates that a corner surface may be formed at the indicated 45 degree angle measuring 0.005+/−0.002 inches in length at the surface 3R.

The third needle seal embodiment illustrated in connection with FIGS. 3H-3R may be made by forming the t-shaped second part (e.g., 1004 of FIG. 3I) of VESPEL® SCP 5000 material. As described above, the VESPEL® SCP 5000 material may be obtained in cylindrical rods where a disk portion may be cut at a desired thickness. The disk portion may then be further machined to obtain the desired shape and dimensions including the through hole with opening into which the needle is inserted. The first part (e.g., 1002 of FIG. 3I), such as may be made from stainless steel, may be formed to the desired shape and dimensions and may include a throughhole of an appropriate size to accommodate insertion of bottom portion of the second part of VESPEL® SCP 5000 material. The bottom portion 1022b of 1004 made of VESPEL® SCP 5000 material is deformable so that it may be pressure fitted via insertion into a through hole of the first portion 1002 as described above. With reference to element 1110 of FIG. 3M, it should be noted that after the bottom portion of the second part is press-fit into the first part, the bottom surfaces as indicated by 1111 may be machined to be coplanar within 0.0002 inches.

With reference back to FIG. 2B, it should be noted that element 183 refers to a passageway or conduit into which the needle is inserted and may be surrounded by a material 187 such as stainless steel or one of a variety of different suitable PEEK (polyether-ether-ketone) materials known in the art. For example, when using the needle seal of FIGS. 2C-F, an embodiment may form 187 from stainless steel. When using the needle seal of FIG. 3A-3D or 3H-3L, an embodiment may form 187 from stainless steel or a PEEK material. It should be noted that element 1004 of FIG. 3I should have a sufficient diameter and surface area in contact with the surrounding material 187 so that when assembled, the element 1004 retains its shape when subjected to the pressures due to mechanical assembly. Element 189a may be a component holding the seal. Element 189b may be a spacer. Element 189c may be a spring support or cup.

It should be noted that the components of an injection port as of FIGS. 2A and 2B may be included within a housing. The components illustrated in FIGS. 2A and 2B may be made of any suitable material and manufactured using any suitable means and techniques known in the art. For example, as described above, the needle support structure material 187 as well as the connections connecting ports 186a and 186b c to 183 may be made of a PEEK material. The housing may be made of aluminum. The spring 188a, tubing used in connection with 185, and components represented by 189a, 189b and 189c may be made from stainless steel.

As illustrated in connection with FIGS. 2A and 2B, needle seal surfaces are in contact with the passageway 183 and there is a substantially fluid tight connection therebetween. Similarly, there may be substantially fluid tight connections between connections 186c and 183, and between 186d and 183 included in the path of the washing fluid for needle washing. As will be appreciated by those skilled in the art, although not explicitly stated, connections between other components illustrated and described in FIGS. 2A and 2B and others herein may also be characterized as fluid tight so as not to allow undesirable leakage of the sample, washing fluid, and the like.

A needle seal may be formed of different shapes and using other encasings than as described herein. An embodiment of a needle seal in accordance with techniques herein may be formed using the VESPEL® SCP 5000 material or VESPEL® SCP 50094 material at the sealing surface which is contact with the needle tip forming the seal. Such an embodiment of a needle seal may be formed from VESPEL® SCP 5000 material or VESPEL® SCP 50094 material alone (e.g., as in FIGS. 3A-3G), or in combination with other portions formed from other suitable materials so long as the surfaces of the needle seal in contact with the needle tip are formed from VESPEL® SCP 5000 material or VESPEL® SCP 50094 material. More generally, it should be noted that an embodiment of a sealing member, such as a needle seal or rotor, in accordance with techniques herein may have at least the sealing surface (where the static or dynamic seal is formed) made of the VESPEL® SCP 5000 material or VESPEL® SCP 50094 material.

It should be noted that although particular examples of dynamic seals are provided herein, VESPEL® SCP 5000 material and/or VESPEL® SCP 50094 material (or similar polymer that may have other commercial names and/or vendors) may be used in forming other types of static and/or dynamic seals as may be used in connection with an LC system, such as an HPLC or UPLC system. For example, an LC system may include one or more of a needle seal, tube seal, ferrule, gasket (such as a check valve gasket), and the like, made from VESPEL® SCP 5000 material or VESPEL® SCP 50094 material at a surface at which a static or dynamic seal is formed.

What will now be described are other various characteristics of VESPEL® SCP 5000 material and VESPEL® SCP 50094 material as provided by DuPont. It should be noted that other materials may be provided by other vendors and/or be referred to using a different commercial names than as described herein where such materials may have properties and characteristics in accordance with those of VESPEL® SCP 5000 material and VESPEL® SCP 50094 material. Such materials may also be suitable for use in an embodiment of a part or sealing member having a surface thereof which forms a static or dynamic seal. Materials, such as VESPEL® SCP 5000 material and VESPEL® SCP 50094 material, have chemical, mechanical, and other properties which are desirable for use with sealing members forming a dynamic or static seal.

Figure 4:
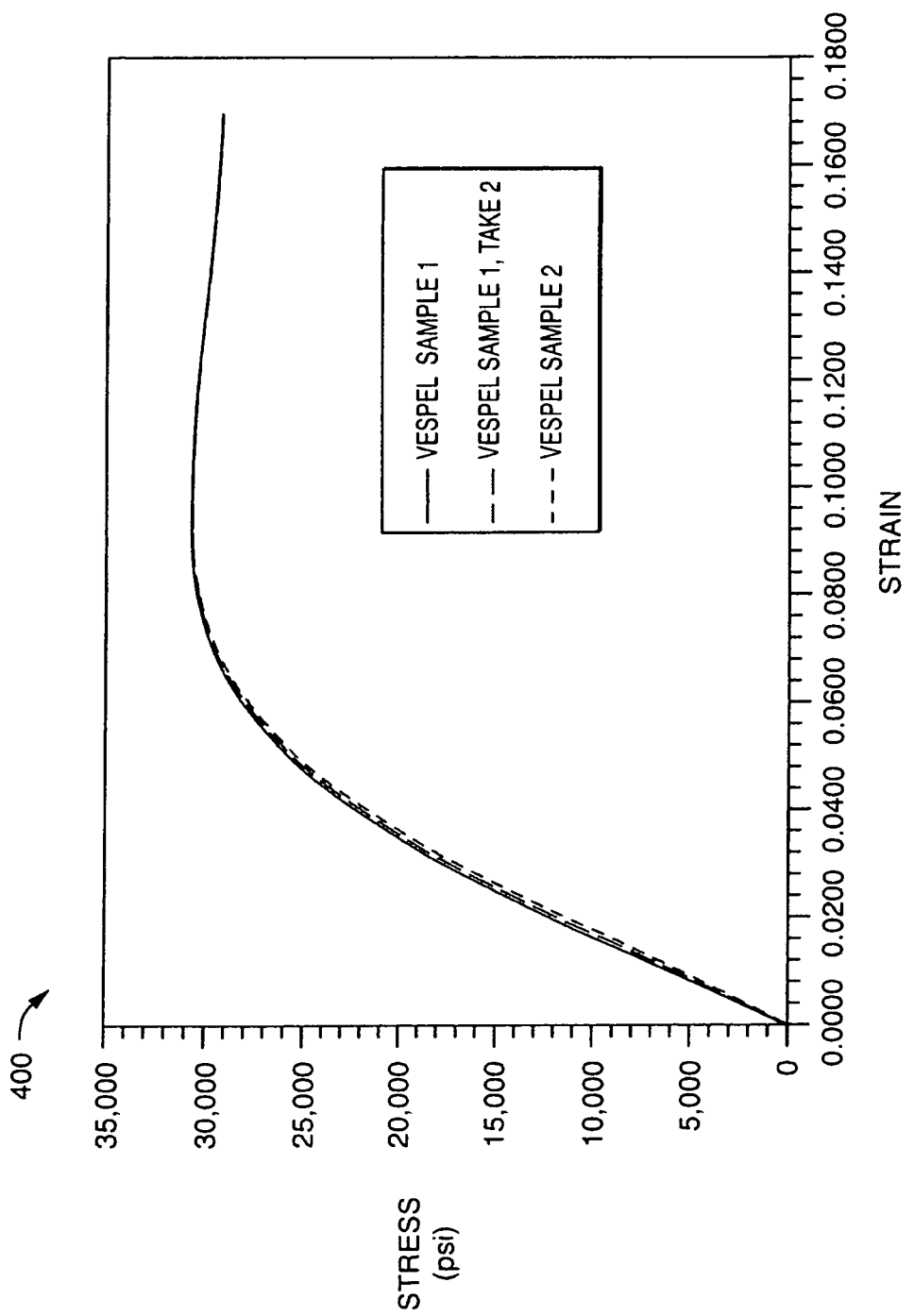
FIG. 4 is a graphical illustration of a stress-strain curve for VESPEL® SCP 5000 material as may be used in an embodiment in connection with techniques herein.

Referring to FIG. 4, shown is a graphical illustration of a stress-strain curve for VESPEL® SCP 5000 material as may be used in an embodiment in accordance with techniques herein. In connection with FIG. 4, stress may be defined as the applied force divided by a cross-sectional area, and strain may be defined as the extension per unit length of the sample. It should be noted that a critical point in connection with FIG. 4 may be characterized as the yield point which is the maximum stress along the linear portion of the illustrated curves. For all the illustrated curves, this is about 30,000 psi which suggests that the material can potentially perform at fluid pressures up to this maximum of about 30,000 psi. The standard test method utilized in connection with producing the curves of FIG. 4 is the standard test method ASTM D695.

It should be noted that FIG. 4 that characterizes isostatically compressed or molded shapes of VESPEL® SCP 5000 material (also referred to as VESPEL® SCP 5000 ISO material).

Referring to FIGS. 5A and 5B, shown are some properties that characterize isostatically compressed or molded shapes of VESPEL® SCP 5000 material (also referred to as VESPEL® SCP 5000 ISO material or SCP 5000 ISO material) as may be used in an embodiment in accordance with techniques herein. The properties are examples of those typical of parts, such as rotors and needle seals, machined from cylindrically shaped rods of VESPEL® SCP 5000 material as described herein. In FIG. 5A, shown are various mechanical properties. In FIG. 5B, shown are various thermal properties, electrical properties, wear properties and other properties.

In following paragraphs, FIGS. 5C-5I and 6A-6F set forth other properties of VESPEL® SCP 5000 ISO material as may be used in an embodiment in accordance with techniques herein.

Figure 5C:
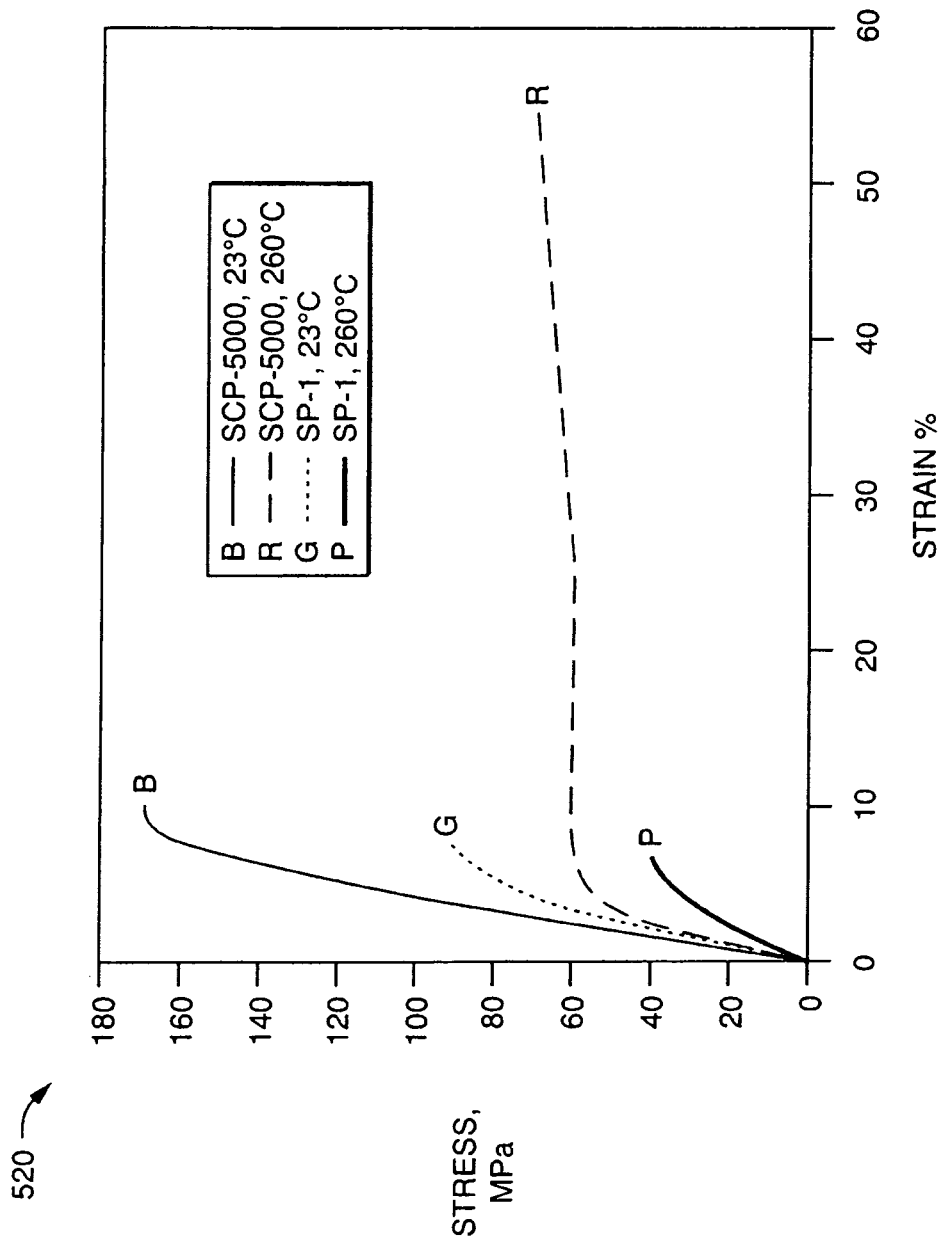

Referring to FIG. 5C, shown is the a graphical illustration of the tensile strength of VESPEL® SCP 5000 ISO material in relation to SP-1. At room temperature, SCP 5000 material illustrates almost twice the strength and similar elongation as SP-1. At 260 degrees Celcius, SCP 5000 exhibits about 50% more strength and greater elongation characteristics.

Figure 5D:
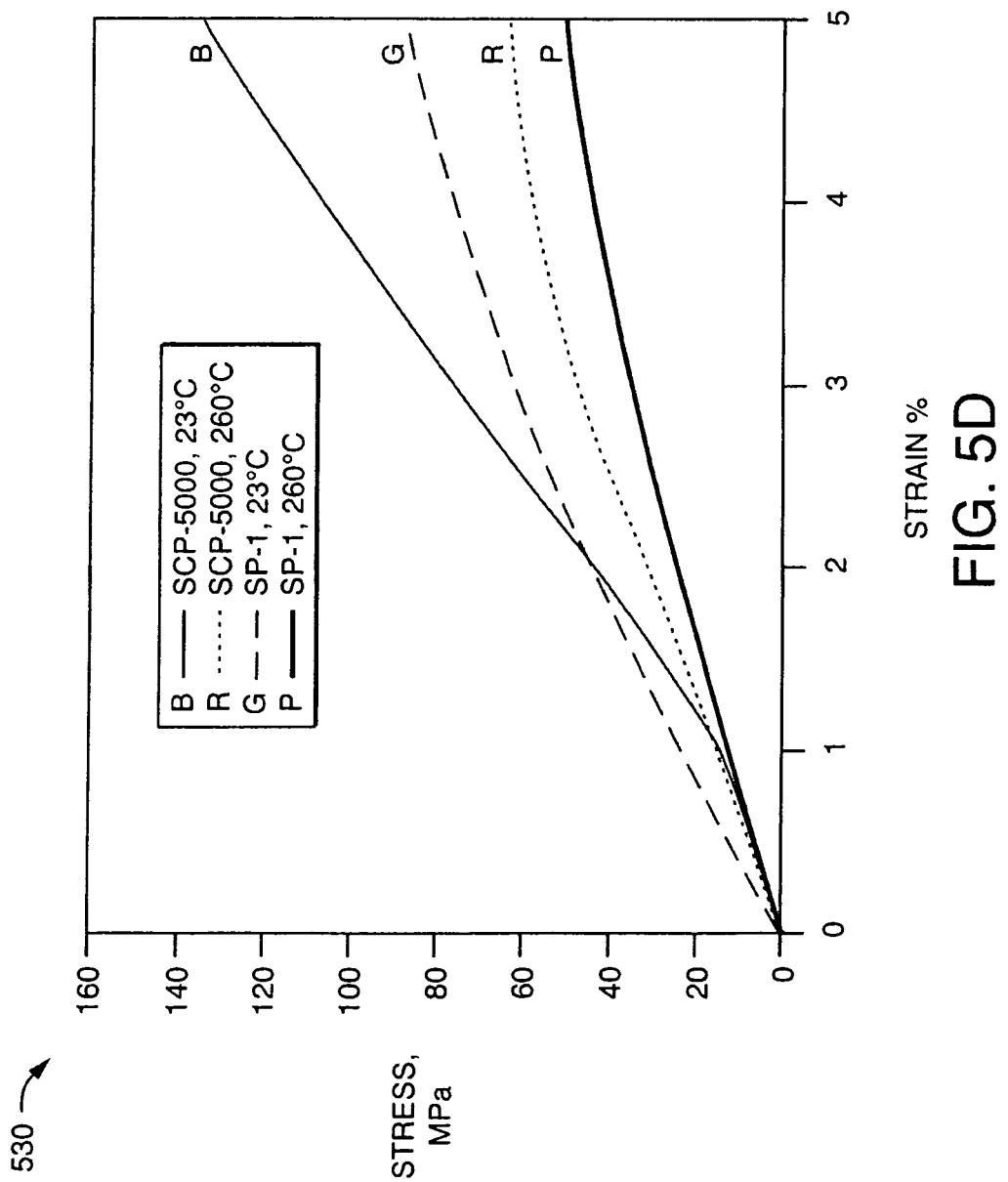

Referring to FIG. 5D, shown is a graphical illustration of the stress-strain curve for the SCP 5000 ISO and SP-1 materials under compression. As illustrated in FIG. 5D, SCP 5000 material exhibits higher compression strength than SP-1 material at both room and elevated temperature.

FIGS. 5C and 5D characterize physical properties of SCP 5000 ISO material. It should be noted that SCP 5000 material does not melt and has a glass transition temperature of 330 degrees Celcius.

Figure 5E:
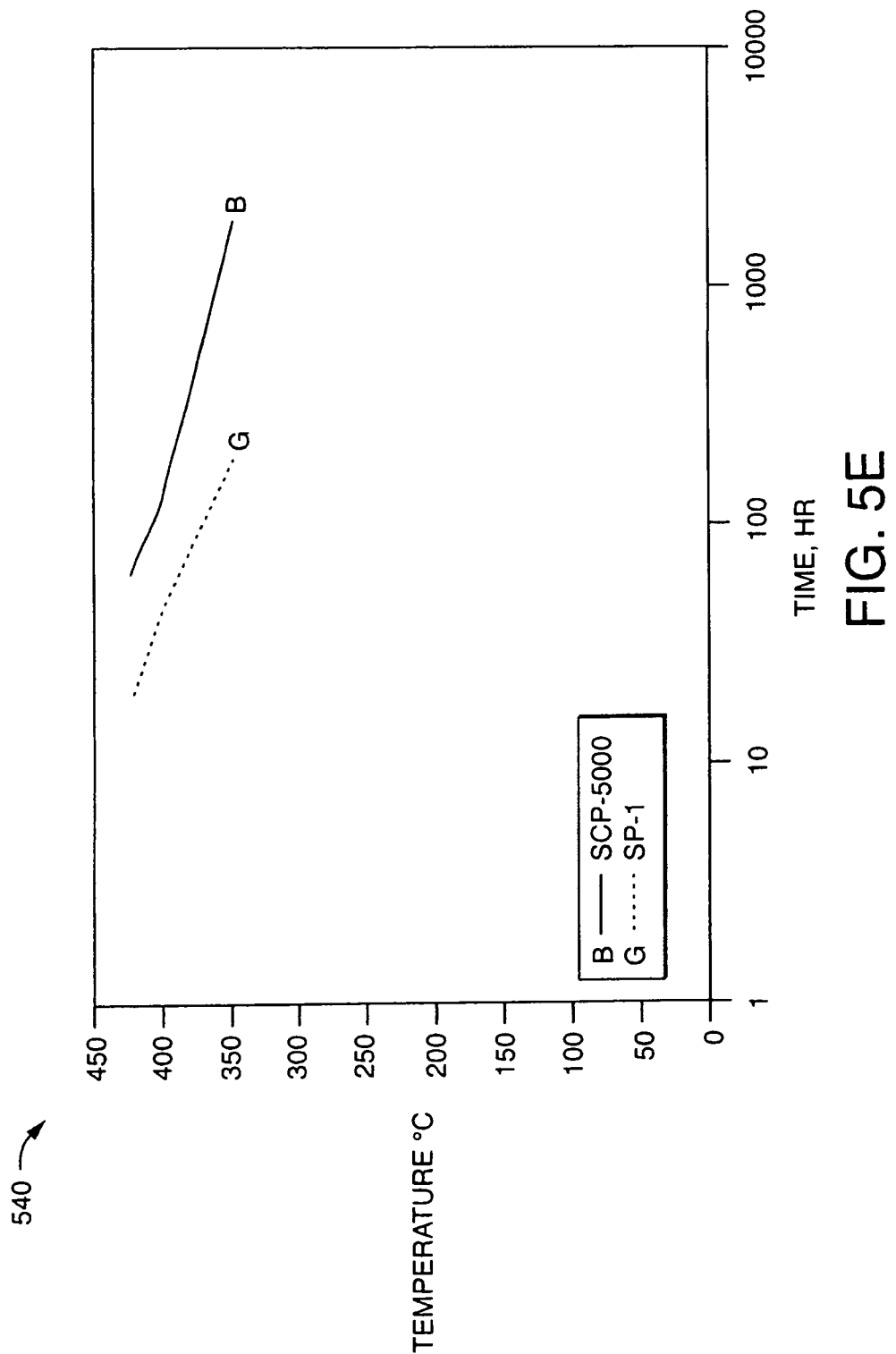

Referring to FIG. 5E, shown is a graphical illustration of thermal properties of SCP 5000 ISO material in relation to SP-1 material. FIG. 5E illustrates characteristics of SP 5000 material as compared to SP-1 polyimide material at high temperatures in terms of time to 50% reduction in initial tensile strength. For example, after 100 continuous hours exposure to air at 370 degrees Celcius, SP-1 will retain half its initial strength. In contrast, under the same conditions, SCP 5000 material will last about 550 hours before its initial strength is reduced by 50%. At temperatures up to at least 340 degrees Celcius, SCP parts perform in inert environments such as nitrogen or vacuum with negligible loss of properties with time. It should be noted that the illustration in FIG. 5E is more generally a guide and that actual useful service life of parts made with SCP 5000 material may be greater due to the fact that temperatures encountered may be intermittent rather than continuous and also that parts may be at least partially covered by housing rather than being totally exposed to air in high temperature applications.

Figure 5F:
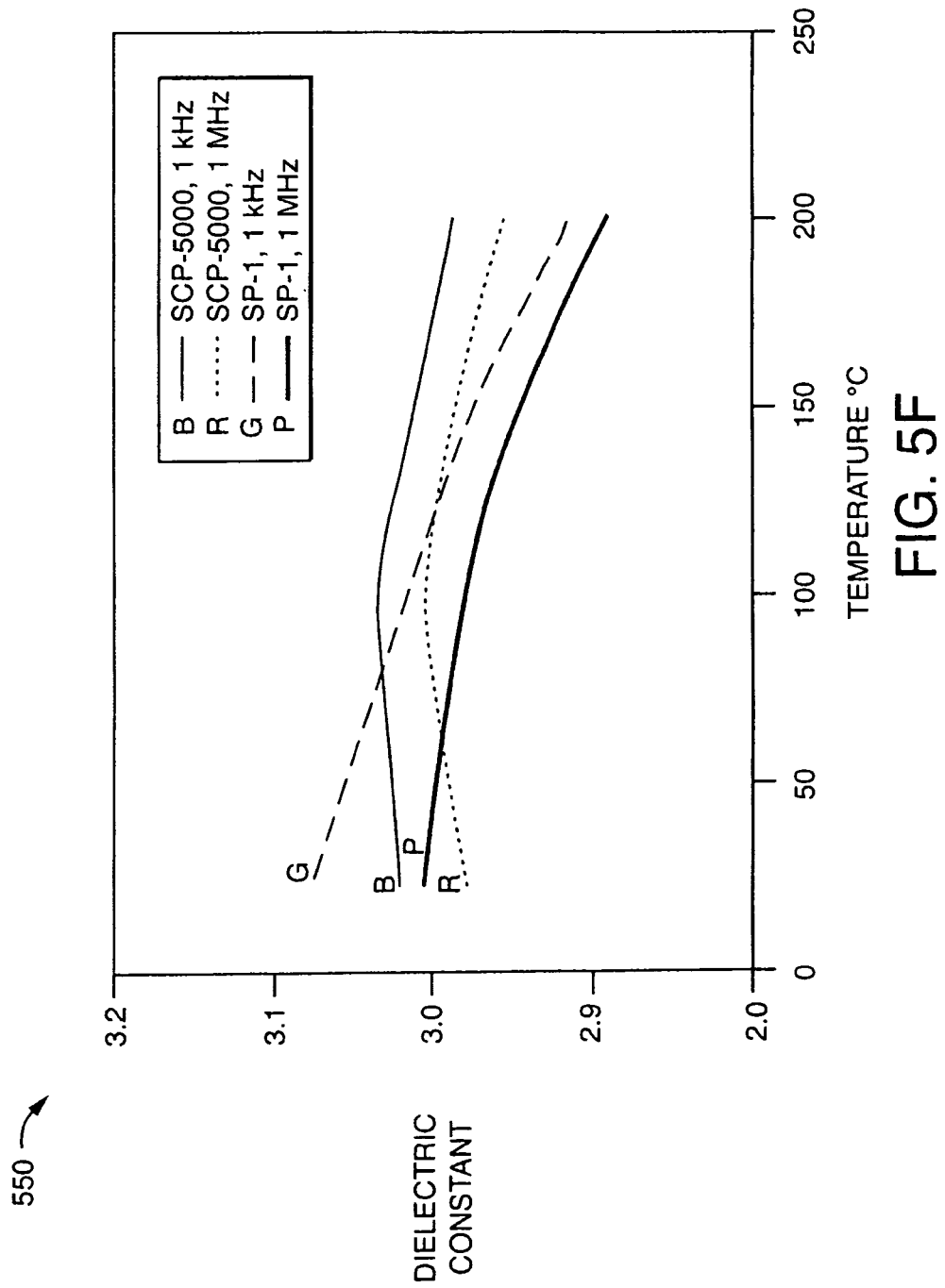
Figure 5G:
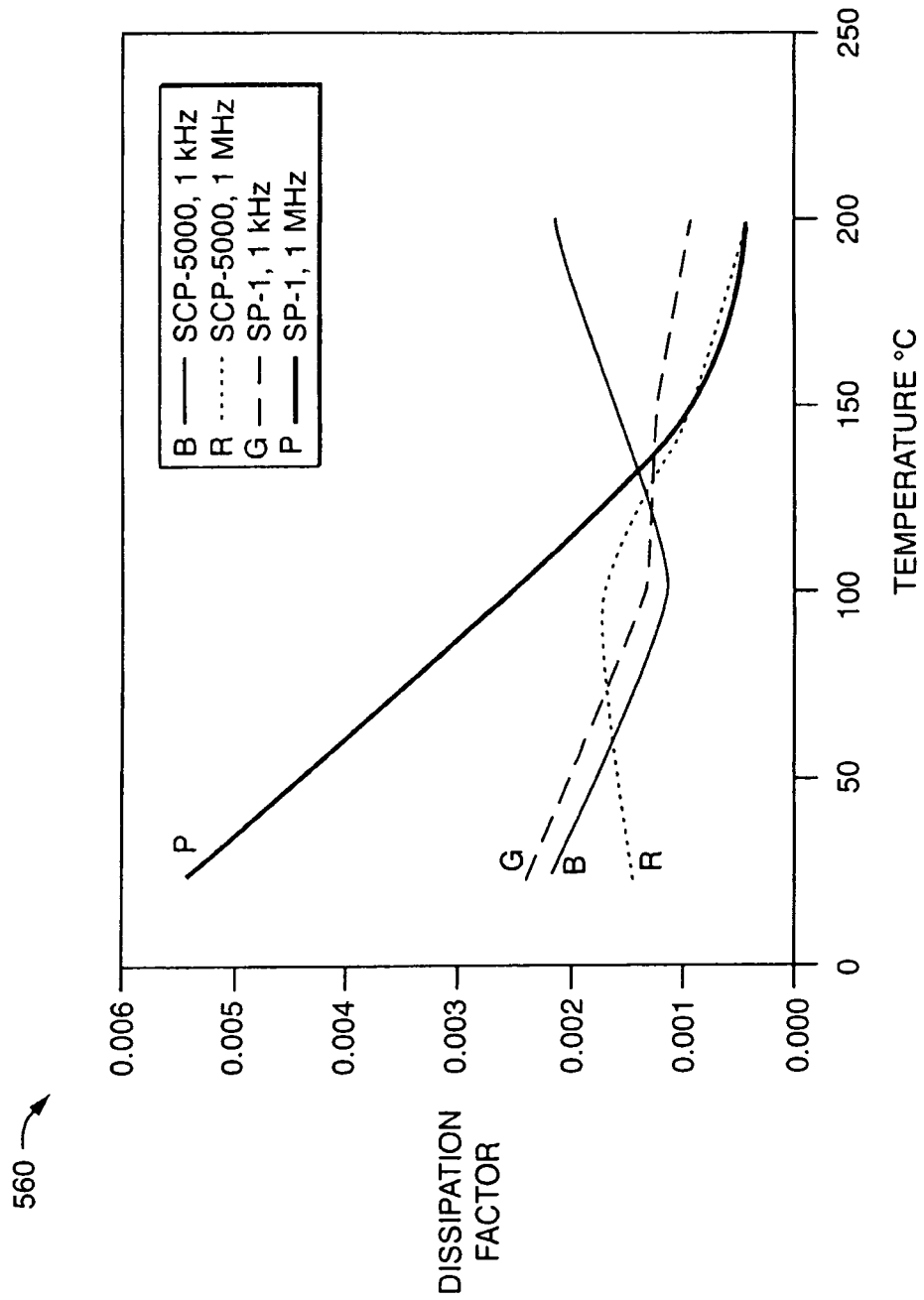

The following FIGS. 5F, 5G and 5H illustrate electrical properties of SCP 5000 ISO material as may be used in an embodiment in accordance with techniques herein.

Referring to FIG. 5F, shown is a graphical illustration of the dielectric constant for SCP 5000 ISO material in comparison to SP-1 material as a function of temperature and frequency. As illustrated, SCP 5000 material exhibits a more stable dielectric constant across a broad temperature and frequency range.

Referring to FIG. 5G, shown is a graphical illustration of the dissipation factor for SCP 5000 ISO material in comparison to SP-1 material.

Referring to FIG. 5H, shown is a graphical illustration of the dielectric strength for SCP 5000 ISO material in comparison to SP-1 material. For a 1.0 mm thick sample, test results indicate that SP-1 and SCP 5000 materials exhibit dielectric strength that is stable across a broad temperature range with SCP 5000 material exhibiting slightly higher dielectric strength than SP-1 material. The table 572 also included in FIG. 5I illustrates the surface and volume resistivity of SCP 5000 material as compared to SP-1 material.

Figure 6B:
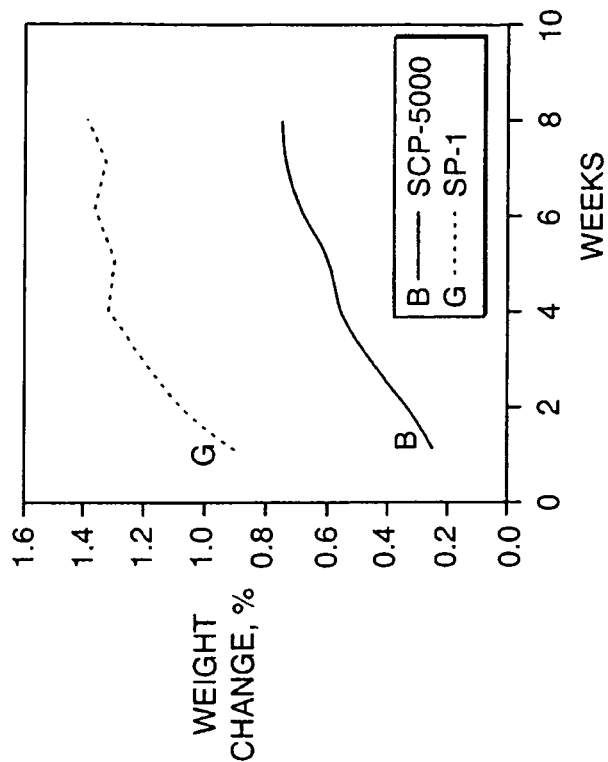
Figure 6A:
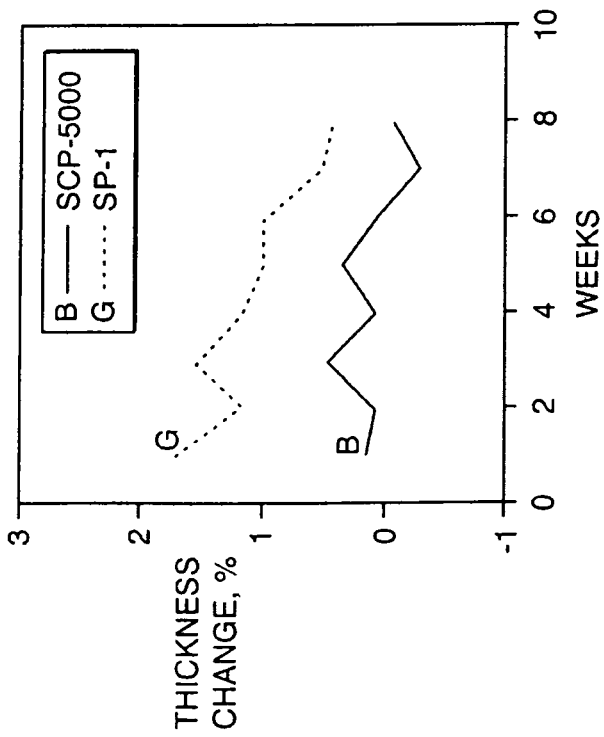

The following FIGS. 6A and 6B illustrate dimensional stability of SCP 5000 ISO material as may be used in an embodiment in accordance with techniques herein.

Referring to FIG. 6A, shown is a graphical illustration of dimensional stability of SCP 5000 material in comparison to SP-1 material when exposed to 100 degrees F. and 90% relative humidity in a controlled environment chamber.

Referring to FIG. 6B, shown is a graphical illustration of specimen weight gain of SCP 5000 material in comparison to SP-1 material under the controlled environment conditions as described for FIG. 6A. FIG. 6B shows the percent weight gain of the sample over time with SCP 5000 material exhibiting about 50% less moisture uptake in comparison to SP-1 material.

It should be noted that, as with polyimides, SCP 5000 and SP-1 material are subject to hydrolysis and severe cracking may occur in water or steam at temperatures exceeding 100 degrees Celcius.

Figure 6C:
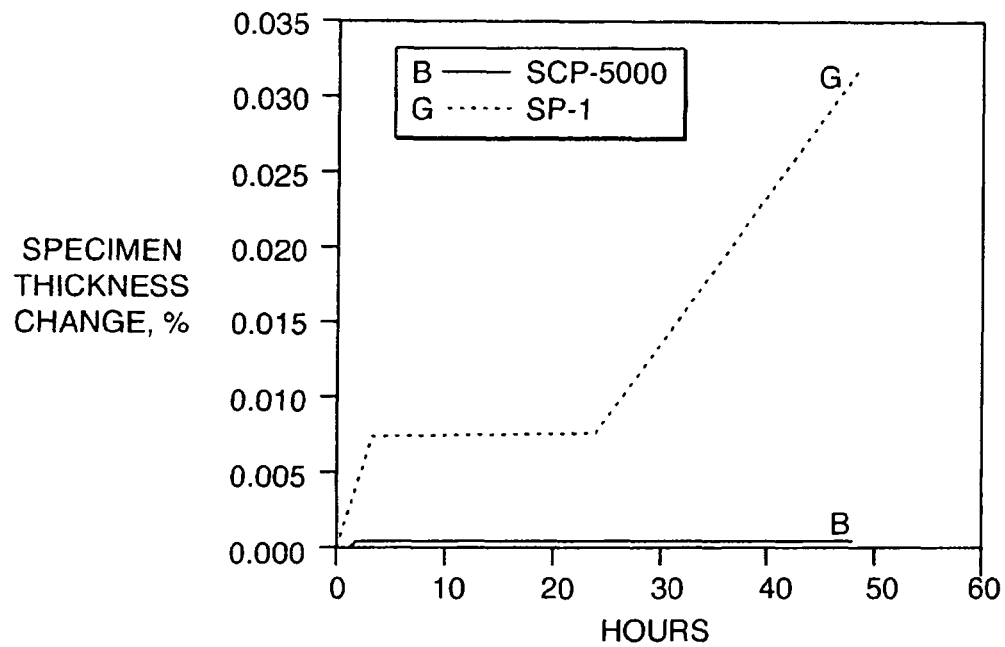
Figure 6D:
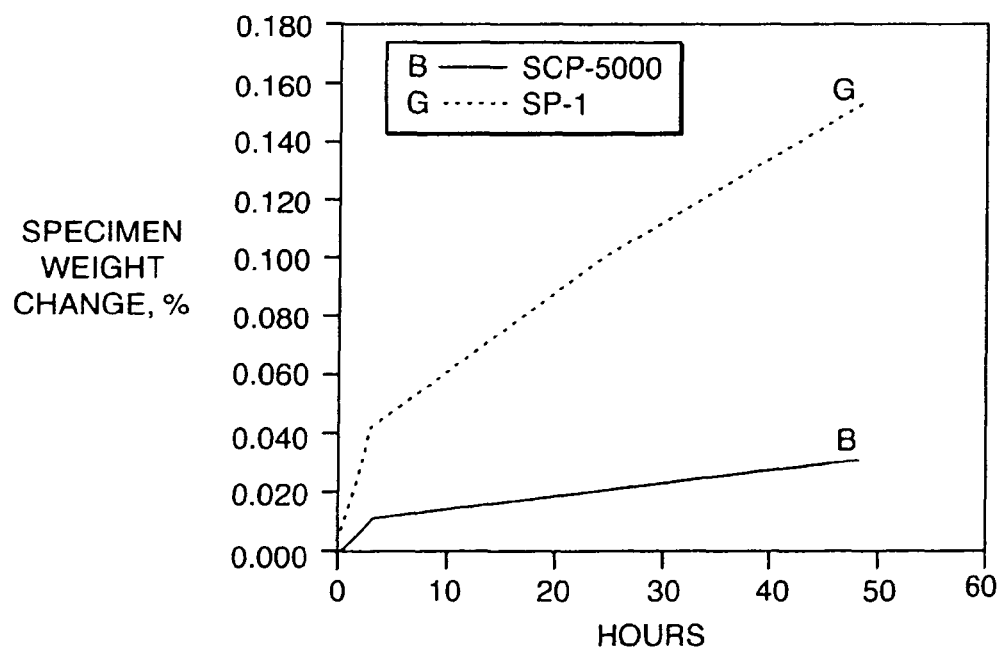
Figure 6E:
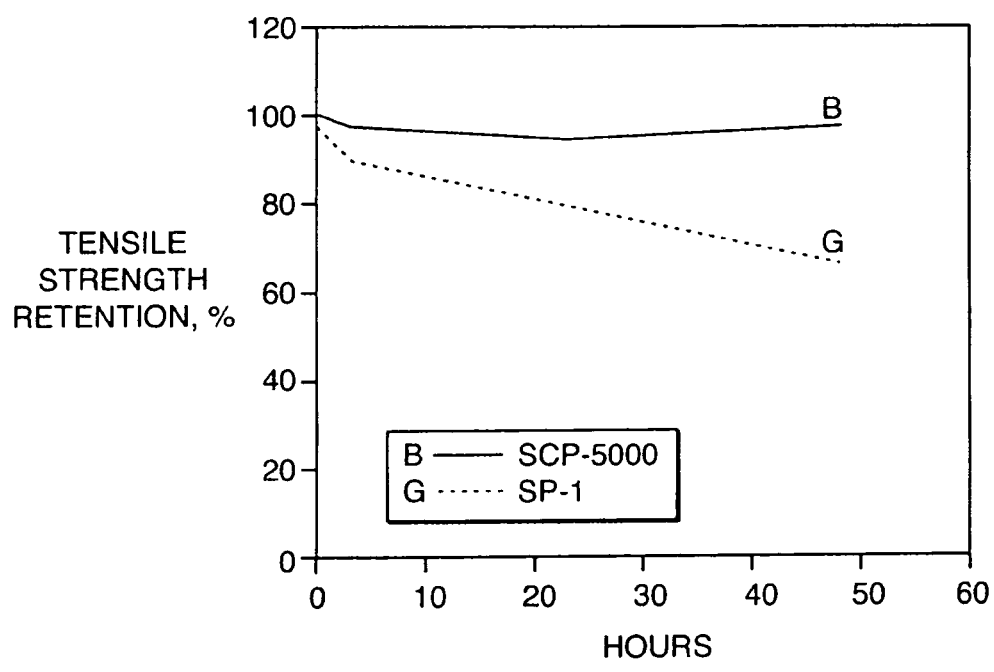

The following FIGS. 6C, 6D and 6E graphically illustrate properties of SCP 5000 ISO material in comparison to SP-1 material with respect to the effect of Anhydrous Ammonia Vapor exposure. After more than 40 hours of exposure, SCP 5000 specimens exhibited no change in thickness (FIG. 6C) and minimal weight gain (FIG. 6D). Additionally, SCP-5000 material retains nearly all of its initial strength (FIG. 6E).

It should be noted that organic solvents generally have minimal effect on the mechanical and dimensional stability of polyimide parts. Chlorinated and fluorinated solvents, such as perchloroethylene and trichloroethylene, are recommended for surface cleaning. Hydrocarbon solvents such as toluene and kerosene have virtually no effect on polyimide materials. At high temperatures, some solvents containing functional groups such as m-cresol and nitrobenzene can cause swelling of polyimides without substantially reducing its mechanical strength.

Concentrated mineral acids may cause severe embrittlement of polyimide parts in a relatively short time. Generally, dilute acid solutions and aqueous solutions of inorganic salts having acidic pH's have about the same effect on a polyimide as water. Generally, polyimide resins are susceptible to alkaline attack. Aqueous bases attack polyimides leading to a rapid deterioration of properties. All basic solutions having a pH of 10 or greater, including salt solutions, may therefore not be preferred for use with SCP 5000 parts.

Referring to FIGS. 6F and 6G, shown in tabular form are additional properties typical of isostatically compressed shapes formed with SCP 5000 ISO.

What will now be described and illustrated are properties of VESPEL® SCP 50094 material.

Referring to FIGS. 7A-7D, shown in tabular form are properties of direct formed (DF) parts made from VESPEL® SCP 50094 material sold by DuPont™. As will be appreciated by those skilled in the art, direct formed refers to another way in which parts are produced as opposed to machining. As known in the art, direct formed refers to forming near net shape parts with a thermoset material. FIGS. 7A-7B illustrate mechanical properties of polyimide DF parts made of VESPEL® SCP 50094 material. FIGS. 7C-7D illustrate thermal, electrical and wear properties of polyimide DF parts made of VESPEL® SCP 50094 material.

Figure 7E:
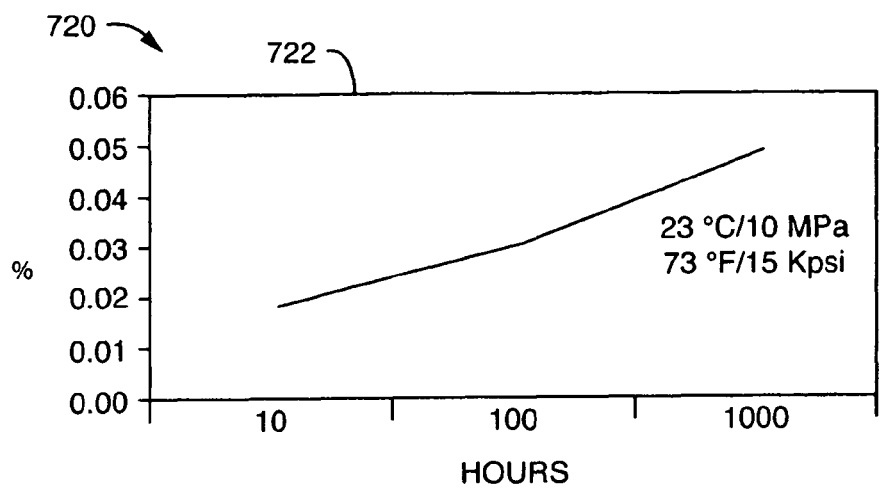
Figure 7F:
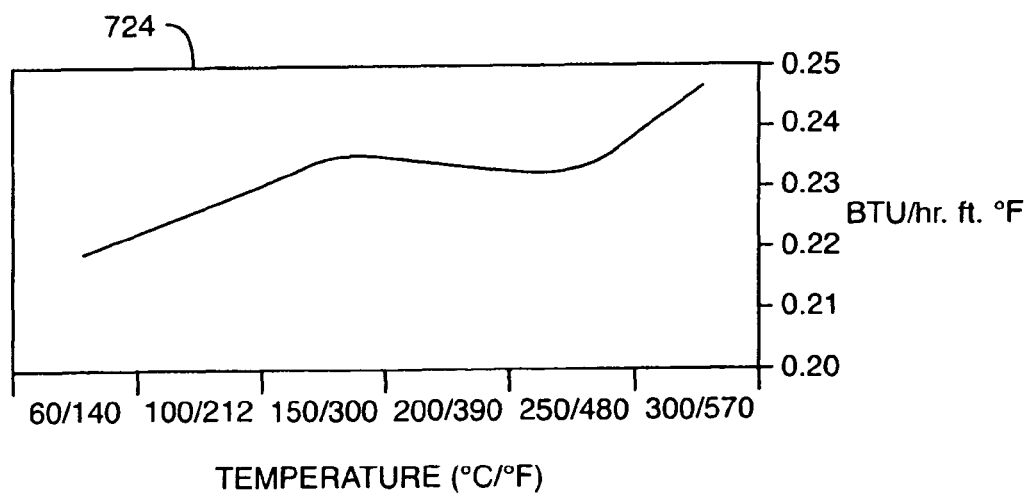

Referring to FIGS. 7E-7F, shown are graphical illustrations of additional properties of DF parts made of VESPEL® SCP 50094 material. FIG. 7E includes a first graph 722 illustrating compressive creep and FIG. 7F includes a second graph 724 illustrating thermal conductivity.

Referring to FIGS. 7G, 7H and 7I, shown in tabular form are properties of parts made from SCP 50094 that characterize isostatically compressed or molded shapes of VESPEL® SCP 50094 material (VESPEL® SCP 50094 ISO material). FIGS. 7G-7H illustrate mechanical properties of parts made of isostatically compressed or molded VESPEL® SCP 50094 material (VESPEL® SCP 50094 ISO material). FIG. 7I illustrates thermal, wear, and other properties of parts made of isostatically compressed or molded VESPEL® SCP 50094 material (VESPEL® SCP 50094 ISO material).

Figure 8A:
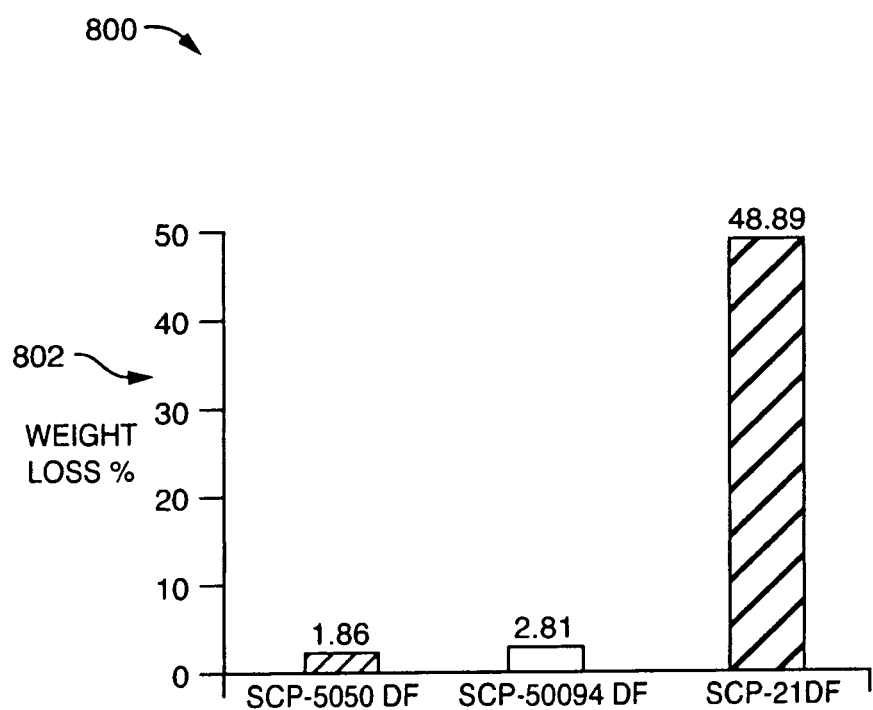
Figure 8B:
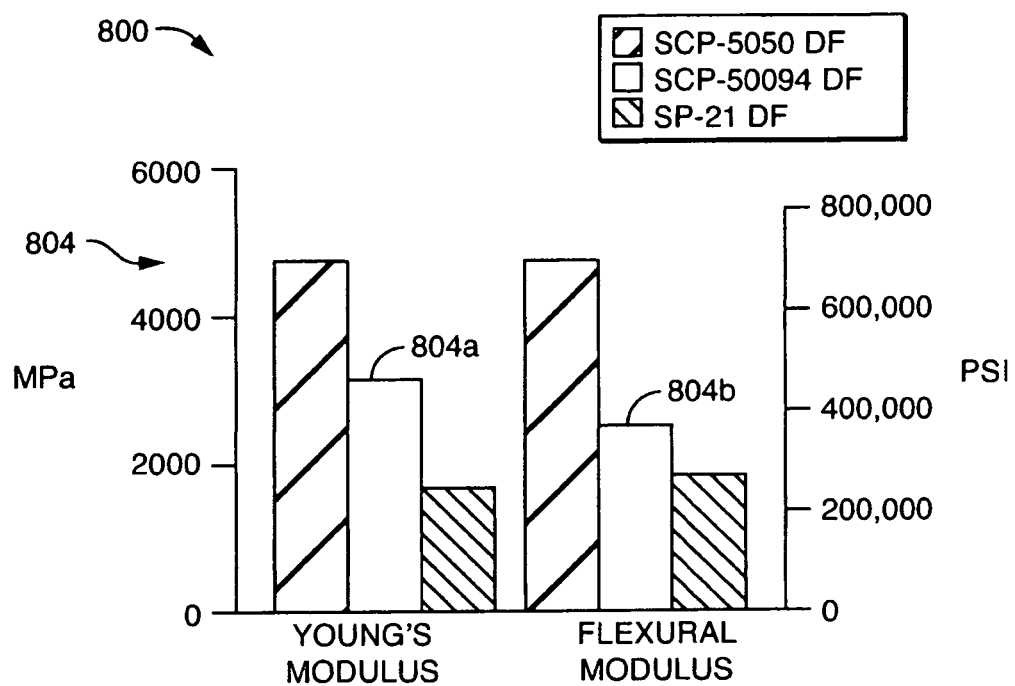
Figure 8C:
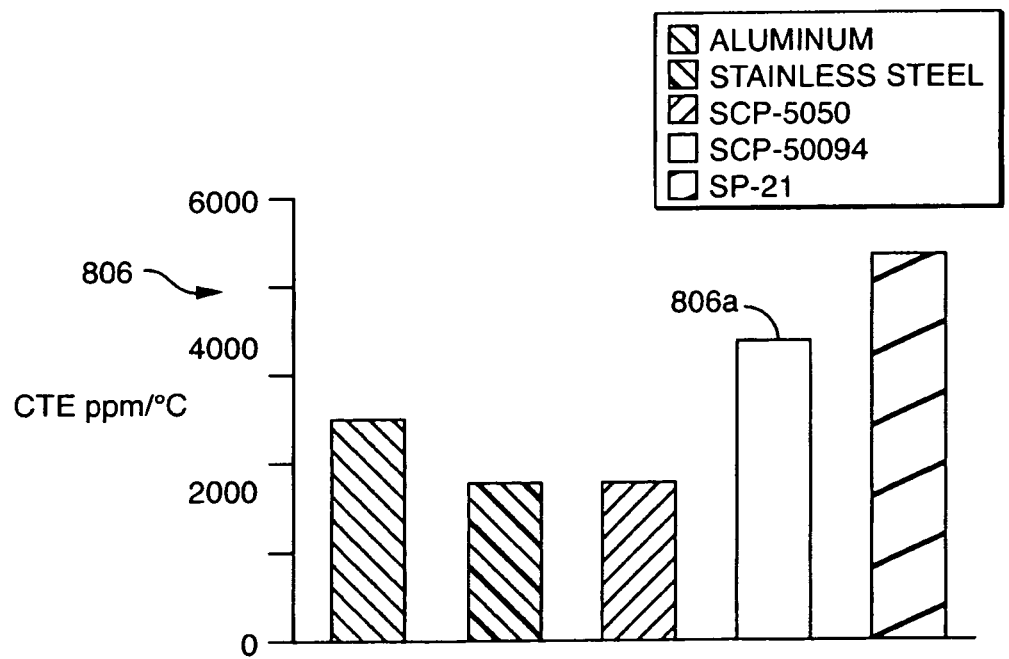

Referring to FIGS. 8A-8C, shown are various properties of SCP 50094 in comparison to other materials. Element 802 is a graphical illustration of the thermal oxidative stability of SCP 50094 DF material in comparison to other materials where the sample was exposed to conditions of 371 degrees Celcius at 4.76 atm (70 psia) for a time period of 100 hours. Under such conditions, the sample made of SCP 50094 material experienced a weight loss of 2.81%. Element 804 is a graphical illustration of Young's modulus and Flexural modulus of SCP 50094 DF material (denoted as 804a and 804b) in comparison to other materials. Element 806 is a graphical illustration of the coefficient of thermal expansion of SCP 50094 material (denoted as 806a) in comparison to other materials.

Figure 8E:
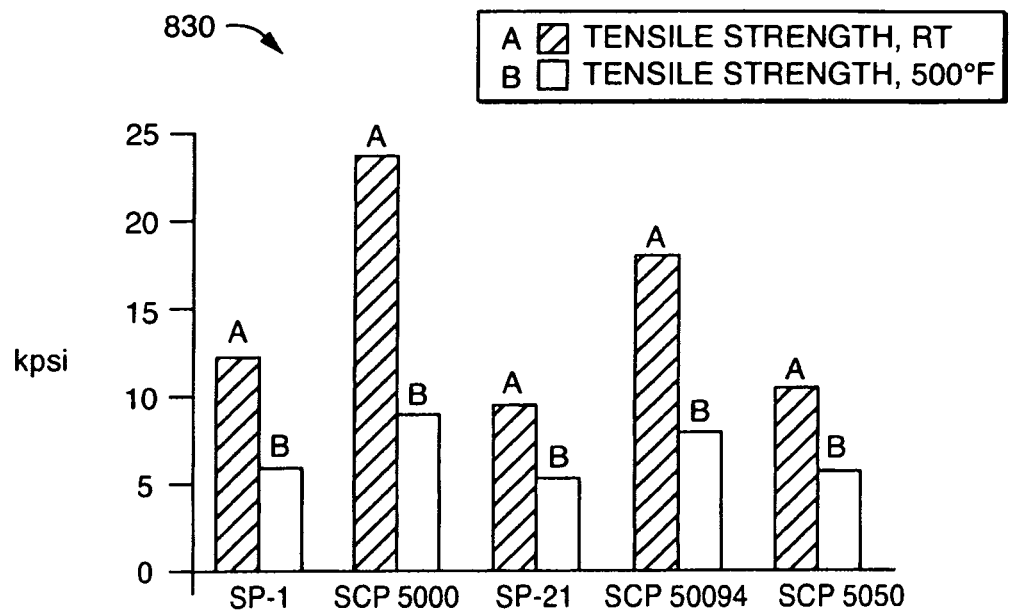
Figure 8F:
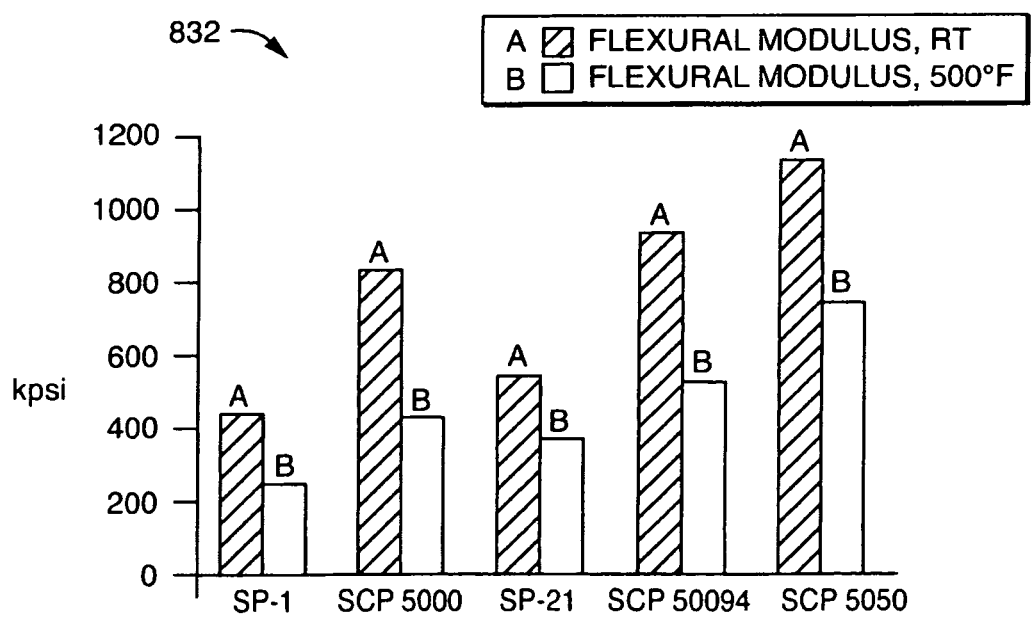

Referring to FIGS. 8D-8F, illustrated are additional various properties of VESPEL® SCP 5000 material and SCP 50094 material in comparison to other VESPEL® materials of isostatic shape grades (ISO). The illustration 820 includes exemplary mechanical, friction and other properties in tabular form 822. Element 826 denotes properties of SCP 5000 material and element 828 denotes properties of SCP 50094 material. Also included are graphical representation 830 of tensile strength in FIG. 8E and a graphical representation 832 of flexural modulus in FIG. 8F where A denotes the material at room temperature (RT) and B denotes the material at 500 degrees Fahrenheit.

Referring to FIGS. 9A, 9B and 9C, shown are tables of solvents as tested by the inventors which have been determined as compatible for use with VESPEL® SCP 5000 material. The test samples are cylinders which are 0.40 inches long and 0.25 inches in diameter (as indicated in testing guidelines). The test samples were observed for a time period of 4 weeks and were placed in testing containers containing the indicated solvents. The testing indicated no visual change to the solution or material and there was no significant change to mass or shape when the samples were removed.

Materials such as VESPEL® SCP 5000 material and/or SCP 50094 material have properties as described herein which are desirable for use in connection with forming a sealing member, such as a rotor or needle seal in connection with LC systems as well as other applications. Characteristics, such as superior strength and wear as well as a high level of chemical compatibility in comparison to other polymers used for similar sealing applications, are some of those which may be highly desirable of materials used in forming static and/or dynamic sealing members in a variety of different applications such as, for example, a UPLC or HPLC system as described herein. Other properties considered in connection with selection of a material may relate to the ability of the material to form an adequate seal such as may be related to porosity process issues (e.g., condition of surfaces at which seals are formed) and the ability of the material to be reinforced, such as by carbon, glass or other suitable reinforcement known to those of ordinary skill in the art.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. A sealing member forming a dynamic seal at a surface thereof, the sealing member having at least the surface thereof formed from one of an unfilled thermoset polyimide polymer or a thermoset polyimide polymer with a graphite filler, wherein the sealing member is a needle seal comprising a first portion and a second portion, said first portion having a t-shaped profile with a through hole formed therethrough, an inner surface of the through hole being the surface at which the dynamic seal is formed when the inner surface is in contact with a needle tip inserted into the through hole, wherein the first portion includes a top portion and a bottom portion, wherein said top portion has a cylindrical shape and said bottom portion is inserted into said second portion of the needle seal, wherein said through hole includes an inwardly tapered portion, wherein said second portion is formed from stainless steel.

2. The sealing member of claim 1, wherein the sealing member forms the dynamic seal in a liquid chromatography system.

3. The sealing member of claim 1, wherein the needle seal is included in an injector used to inject a sample into a liquid chromatography system.

4. The sealing member of claim 1, wherein the first portion is formed from said unfilled thermoset polyimide polymer.

5. The sealing member of claim 4, wherein a first portion of the through hole tapers inwardly with respect to an opening at a first end of the through hole into which a needle having the needle tip is inserted, and wherein a second portion of the through hole is untampered and is adjacent to the first portion of the through hole, and wherein the through hole includes another tapered portion adjacent to the second portion of the through hole, the other tapered portion forming a conical portion at a second end of the through hole opposing the first end.

6. The sealing member of claim 1, wherein said second portion is formed from a material having mechanical properties indicating that the second portion has a mechanical strength which is greater than the first portion.

7. The sealing member of claim 1, wherein the sealing member is included in an apparatus also comprising an injection port, and the sealing member is separate from the injection port.

8. The sealing member of claim 1, wherein the through hole further includes another portion having a relatively uniform diameter.

9. The sealing member of claim 1, wherein a needle having the needle tip, when inserted into the through hole, does not extend completely through the through hole when the dynamic seal is formed.

* * * * *